(12) United States Patent
Tajima et al.

(10) Patent No.: US 8,414,778 B2
(45) Date of Patent: Apr. 9, 2013

(54) FILTRATION METHOD, FILTER-INCORPORATED TIP, AND FILTRATION DEVICE

(75) Inventors: Hideji Tajima, Chiba (JP); Tomoyuki Hatano, Chiba (JP); Masataka Fumoto, Chiba (JP); Yoshinori Koh, Chiba (JP); Tomomi Saegusa, Chiba (JP)

(73) Assignee: Universal Bio Research Co., Ltd., Matsudo-shi, Chiba (JP)

( * ) Notice: Subject to any disclaimer, the term of this patent is extended or adjusted under 35 U.S.C. 154(b) by 0 days.

(21) Appl. No.: 11/920,707

(22) PCT Filed: May 17, 2006

(86) PCT No.: PCT/JP2006/309815
§ 371 (c)(1),
(2), (4) Date: Aug. 6, 2009

(87) PCT Pub. No.: WO2006/123688
PCT Pub. Date: Nov. 23, 2006

(65) Prior Publication Data
US 2009/0294385 A1    Dec. 3, 2009

(30) Foreign Application Priority Data
May 17, 2005 (JP) ................................. 2005-144728

(51) Int. Cl.
*B01D 37/04* (2006.01)
(52) U.S. Cl. ........ 210/744; 210/741; 210/103; 210/104; 210/808; 210/138; 435/287.2; 422/501; 422/511; 422/513; 422/524; 422/527; 422/534; 422/522
(58) Field of Classification Search .................... None
See application file for complete search history.

(56) References Cited

U.S. PATENT DOCUMENTS 5,378,360 A * 1/1995 Huse et al. ................. 210/198.2
5,876,605 A * 3/1999 Kitajima et al. .............. 210/650
(Continued)

FOREIGN PATENT DOCUMENTS

| EP | 1469068 | 10/2004 |
| EP | 1519196 | 3/2005 |

(Continued)

OTHER PUBLICATIONS

Millipore Corporation, "Microcon® Centrifugal Filter Devices User Guide," Mar. 2000, 26 pages.
(Continued)

*Primary Examiner* — Robert James Popovics
(74) *Attorney, Agent, or Firm* — Haynes and Boone, L.L.P.

(57) ABSTRACT

The present invention relates to a filtration method, a filter-incorporated tip and a filtration device, and its object is to perform efficient and swift isolation of a target substance. The filtration method therefore comprises: a liquid introducing step to introduce a liquid into a filter-incorporated tip through a guide opening portion thereof, wherein the filter-incorporated tip has a nozzle-tipped container and a filter, the nozzle-tipped container has a guide opening portion that can be directly or indirectly fitted to an air nozzle capable of ejecting a gas and a front nozzle portion capable of delivering the liquid by the ejection of the gas from the air nozzle, and the filter is locked in the nozzle-tipped container to partition the interior of the nozzle-tipped container into the guide opening portion side and the front nozzle portion side and is adapted to temporarily hold the liquid and isolate a predetermined substance as the liquid passes through the filter, with the nozzle-tipped container coupled to the air nozzle on the guide opening side; a coupling step to directly or indirectly couple the filter-incorporated tip containing the liquid to the air nozzle; and a pressure application step to eject the gas from the air nozzle into the coupled filter-incorporated tip.

16 Claims, 12 Drawing Sheets

U.S. PATENT DOCUMENTS

| | | | |
|---|---|---|---|
| 5,895,631 A * | 4/1999 | Tajima | 422/513 |
| 5,979,669 A * | 11/1999 | Kitajima et al. | 210/455 |
| 5,996,811 A * | 12/1999 | Kitajima et al. | 210/488 |
| 6,045,699 A * | 4/2000 | Yazawa et al. | 210/637 |
| 6,100,094 A * | 8/2000 | Tajima | 436/54 |
| 6,117,394 A * | 9/2000 | Smith | 422/513 |
| 6,159,368 A * | 12/2000 | Moring et al. | 210/321.75 |
| 6,225,130 B1 * | 5/2001 | Kitajima et al. | 436/177 |
| 6,241,947 B1 * | 6/2001 | Komatsu et al. | 422/67 |
| 6,375,855 B1 * | 4/2002 | Vassarotti | 210/787 |
| 6,379,565 B1 * | 4/2002 | Guirguis et al. | 210/767 |
| 6,383,818 B1 * | 5/2002 | Arai et al. | 436/177 |
| 6,455,325 B1 * | 9/2002 | Tajima | 436/526 |
| 6,641,782 B1 * | 11/2003 | Mauchan et al. | 422/52 |
| 6,659,975 B2 * | 12/2003 | Amano et al. | 604/48 |
| 6,783,732 B2 * | 8/2004 | Madden et al. | 422/63 |
| 6,905,825 B2 * | 6/2005 | Kojima et al. | 536/25.4 |
| 7,059,480 B2 * | 6/2006 | Seshimoto et al. | 210/406 |
| 7,682,818 B2 * | 3/2010 | Mori et al. | 435/287.2 |
| 7,927,810 B2 * | 4/2011 | Togawa et al. | 435/7.1 |
| 7,951,335 B2 * | 5/2011 | Tajima | 422/504 |
| 7,951,336 B2 * | 5/2011 | Tajima | 422/504 |
| 7,993,847 B2 * | 8/2011 | Togawa et al. | 435/7.1 |
| 8,057,760 B2 * | 11/2011 | Tajima | 422/547 |
| 2002/0102563 A1 * | 8/2002 | Gjerde et al. | 435/6 |
| 2002/0182718 A1 * | 12/2002 | Malmquist | 435/287.2 |
| 2002/0192667 A1 * | 12/2002 | Kojima et al. | 435/6 |
| 2003/0039589 A1 * | 2/2003 | Smith | 422/100 |
| 2004/0060859 A1 * | 4/2004 | Seshimoto et al. | 210/416.1 |
| 2004/0235025 A1 * | 11/2004 | Mori et al. | 435/6 |
| 2005/0123457 A1 * | 6/2005 | Tajima et al. | 422/130 |
| 2006/0014272 A1 * | 1/2006 | Tajima et al. | 435/287.6 |
| 2007/0105156 A1 * | 5/2007 | Togawa et al. | 435/7.1 |
| 2009/0294385 A1 * | 12/2009 | Tajima et al. | 210/808 |
| 2009/0317897 A1 * | 12/2009 | Tajima | 435/287.2 |
| 2010/0119416 A1 * | 5/2010 | Tajima | 422/102 |

FOREIGN PATENT DOCUMENTS

| | | |
|---|---|---|
| EP | 1882524 A1 * | 1/2008 |
| JP | 2-149321 | 6/1990 |
| JP | 2002-528265 | 9/2002 |
| WO | WO 01/88501 | 11/2001 |
| WO | WO 2006123688 A1 * | 11/2006 |

OTHER PUBLICATIONS

International Search Report, issued by the Japanese Patent Office, mailed Jul. 4, 2006, in connection with International Application No. PCT/JP2006/309815.

Written Opinion, issued by the Japanese Patent Office, mailed Jul. 4, 2006, in connection with International Application No. PCT/JP2006/309815.

International Preliminary Report on Patentability, issued by the Japanese Patent Office, mailed Jun. 26, 2007, in connection with International Application No. PCT/JP2006/309815.

Extended European Search Report issued Aug. 5, 2010, by the European Patent Office in connection with EP Application No. 06746518.7.

* cited by examiner

FILTRATION METHOD, FILTER-INCORPORATED TIP, AND FILTRATION DEVICE

CROSS REFERENCE

This application is a United States national phase application of co-pending international patent application number PCT/JP2006/309815, filed May 17, 2006, which claims priority to Japanese patent application number 2005-144728, filed May 17, 2005, the disclosures of which are incorporated herein by reference.

TECHNICAL FIELD

The present invention relates to a filtration method, a filter-incorporated tip and a filtration device.

BACKGROUND ART

In separating or removing a certain substance from a liquid by using a filter that does not let the liquid pass easily therethrough, it is a common practice to use a centrifuge. To process a liquid by the centrifuge, a sample holding container has been in common use which is generally cylindrical and comprises a vial-engaging opening portion at a lower end thereof engageable with an opening portion of a filtered product accommodating glass vial, a sample-introducing opening portion at an upper end thereof into which a sample liquid to be filtered is introduced, a filter provided between the vial-engaging opening portion and the sample-introducing opening portion to separate them from each other, and a cover to hermetically close the sample-introducing opening portion.

To filtrate a biological substance using the sample holding container, the following steps are taken. First, the sample liquid is introduced from the sample-introducing opening portion into a space on the sample-introducing opening portion side of the filter and then the sample-introducing opening portion is closed with the cover. Then, the vial-engaging opening portion is fitted into the opening portion of the glass vial to form an assembly. Next, the sample holding container assembly is mounted in the centrifuge so that the filter is situated on the far side from the sample-introducing opening portion with respect a rotating axis of the centrifuge, with a vertical axis of the container assembly extending in a rotating radial direction perpendicular to the rotary axis of the centrifuge. To strike a balance, another sample holding container assembly is mounted on the opposite side of the rotating axis. Then, the centrifuge is rotated. As a result, the sample liquid that is forced through the filter is received in the glass vials (non-patent document 1).

Non-patent document 1: "MICROCON Centrifugal Filter Devices User Guide" (published by Millipore Corporation, 2000).

The use of a centrifuge that is required in performing filtration using a filter through which a liquid cannot easily pass has a problem of expanding the overall size of the equipment. There is another problem that installing the sample holding container assemblies in the centrifuge can only be done manually, making it difficult to automate a series of operations including preprocessing. Further, a control on the centrifuge can only be performed mainly in terms of only a revolution speed, leaving a fine control impossible. Still another problem is that an appropriate centrifugal force needs to be set according to liquid volumes and filter pore diameters, making the equipment difficult to handle.

It is therefore a first object of this invention to provide a filtration method, a filter-incorporated tip and a filtration device which can perform a process including a filtration with a simple construction without having to expand a size of the device.

A second object is to provide a filtration method, a filter-incorporated tip and a filtration device which can automate an entire series of operations for a process using a filter.

A third object is to provide a filtration method, a filter-incorporated tip and a filtration device which can perform a finely and optimally adjusted process according to a filter used and a liquid being processed.

SUMMARY OF THE INVENTION

Viewed from a first aspect the present invention provides a filtration method comprising: a liquid introducing step to introduce a liquid into a filter-incorporated tip through a guide opening portion thereof, wherein the filter-incorporated tip has a nozzle-tipped container and a filter, the nozzle-tipped container has a guide opening portion that can be directly or indirectly fitted to an air nozzle capable of ejecting a gas and a front nozzle portion capable of delivering the liquid by the ejection of the gas from the air nozzle, and the filter is locked in the nozzle-tipped container to partition the interior of the nozzle-tipped container into the guide opening portion side and the front nozzle portion side and is adapted to temporarily hold the liquid and isolate a predetermined substance as the liquid passes through the filter, with the nozzle-tipped container coupled to the air nozzle on the guide opening portion side; a coupling step to directly or indirectly couple the filter-incorporated tip containing the liquid to the air nozzle; and a pressure application step to eject the gas from the air nozzle into the coupled filter-incorporated tip.

A mechanism or means capable of "ejecting a gas" may, for example, be established by connecting the device to a pump or a mechanism that causes a plunger to slide within a cylinder; by connecting the device to a gas cylinder filled with a compressed gas, such as nitrogen or air, to eject a gas into the filter-incorporated tip, and by connecting the device to an air blowing mechanism using a fan or the like. Particularly by using a gas cylinder of nitrogen gas, a high pressure can be applied to the liquid. Further, where a mechanism is used that can both draw by suction and eject a gas, a pipetting function may be realized by fitting a pipette tip to the device. The "filter" is a penetrative porous solid material having a large number of penetrating holes or gaps of a predetermined size (predetermined pore diameter or predetermined average diameter or length of gaps) through which a liquid is forced to pass to separate, collect or remove a predetermined substance in the liquid. The filter may be shaped like a block, thin film, thin plate, membrane or plate. The filter material includes rubber, silicone, cellulose (including regenerated cellulose), nylon and other fiber materials, resin, non-magnetic particles, magnetic particles and other metals. The material may be in the form of gel, a porous body, a penetrative porous body or a water-containing body. The thin film filter includes, for example, an ultrafiltration membrane for protein filtration or a precision filtration membrane. The "ultrafiltration membrane" refers to a membrane with a pore diameter of between 1 nm to 100 nm while the "precision filtration membrane" refers to a filtration membrane for solute or particles of 0.01 μm to several μm. The "block" shape includes a cylindrical shape, a square pillar shape and a ball shape. The "gas" includes, for example, air, nitrogen, carbon dioxide, oxygen, argon or a gas mixture of two or more of these gases mixed at a variety of ratios.

The "predetermined substance" refers to a substance of a certain molar weight that can be separated by a particular size of pores or gaps of the filter (e.g., the molar weight is appropriate when it is about two times the size of the pores or gaps of the filter). It may be a biological substance including genetic substances such as nucleic acid, and biopolymers or monomers such as protein, sugar, sugar chain, peptide and colorant. The biological substance may include cells, viruses and plasmids. For a protein composed of 1,000 molecules, the size of pores or gaps of the filter will be in a range of between a few nm and a few 10 nm.

The "guide opening portion that can be directly or indirectly fitted to an air nozzle" refers to a procedure of directly fitting the guide opening portion with the nozzle, by engaging, screwing or the like, or indirectly fitting the guide opening portion to the air nozzle through an airpermeable nozzle mounting member, such as tip or adapter. The "tip" has a large-diameter tube and a small-diameter tube communicating with, and formed narrower than, the large-diameter tube. The large-diameter tube has a guide opening portion to be fitted over or engaged with the air nozzle. The small-diameter portion has a front nozzle portion through which a liquid can be drawn in or out by the suction or ejection of air. The small-diameter portion may include, for example, a pipette tip. The engagement of the guide opening portion with the air nozzle is accomplished by, for example, inserting the air nozzle from above into the guide opening portion.

The "nozzle-tipped container" has a guide opening portion and a front nozzle portion and can accommodate the filter. The nozzle-tipped container needs only to have the guide opening portion and the front nozzle portion and a space to temporarily hold a liquid introduced onto the locked filter. The nozzle-tipped container is therefore not limited to the typical tip configuration composed of a large-diameter tube and a small-diameter tube. In the case of a nozzle-tipped container having a large-diameter tube and a small-diameter tube, the filter is installed in a portion corresponding to the large-diameter tube or in a portion corresponding to a transition portion between the large-diameter tube and the small-diameter tube. The nozzle-tipped container preferably has a volume to be able to handle a few μl to a few hundred μl of liquid. The nozzle-tipped container may be formed integral as one piece or formed in two or three separable pieces.

The material of the nozzle-tipped container preferably has a light-transmitting property to allow for an optical observation. The possible materials of the nozzle-tipped container include resins such as polyethylene, polypropylene, polystyrene and acrylics, glass, metals and metal compounds. The size of the nozzle-tipped container may be such that it can accommodate a few μl to a few hundred μl of liquid in the small-diameter tube. During the pressure application process, the front nozzle portion should preferably be positioned above the externally provided container or inserted in it.

The "introduction" is accomplished, for example, by fitting a pipette tip to an air nozzle capable of sucking and ejecting air, drawing a liquid from a container, transferring the liquid to a position where the filter-incorporated tip is installed, and ejecting the liquid into the guide opening portion.

According to a second aspect, the present invention provides a filtration method, wherein a pressure application in the pressure application step that depends on the volume of gas ejected from the air nozzle, gas pressure, speed, the number of ejections, time or position is controlled according to a construction of the air nozzle, a member fitted to the air nozzle or the filter-incorporated tip, according to physical conditions including a kind of substance present in the liquid, a density of the substance, a volume of the liquid and a coordinate position including liquid accommodation position, and according to a content of the process to be performed.

The "content of the process" refers to, for example, pressurization, reaction, washing, transfer, pipetting, separation, extraction, heating, cooling, settling, measuring, mixing, isolation, elution, stirring, etc. or a combination of these operations, including repetitions, performed according to an object of process and according to a predetermined order or a predetermined schedule. The "time" includes a duration of time or timing in or at which suction and ejection are performed. By setting the duration of time or timing, the suction and ejection can be executed intermittently, continuously or discontinuously.

In the case of the "reaction" process, the suction and ejection are repetitively performed according to the material condition by using the liquid in an amount about 80% of the pipette tip volume at a predetermined speed dependent on the material condition and at a container position where the associated reagent is accommodated. The number of suction and ejection operations is also controlled according to the material condition. In the "washing" process, the suction and ejection are repetitively performed a predetermined number of times according to the material condition at a predetermined speed dependent on the process and at a container position where the cleaning liquid is accommodated. In the subsequent processes, the suction and ejection operations are similarly controlled according to the process being executed.

The "speed" varies according to pore diameters of the filter used, a concentration, viscosity, volume and process duration of the liquid and the kind of a substance being processed. When a pipette tip is used for the process and the substance being handled is DNA, the speed needs to be increased to enhance an encounterability because its size is smaller than proteins. The speed also varies depending on the content of the process. In the case of washing and stirring operations, for example, the suction/ejection speed is slower than when a reaction operation is performed. Where the filter is an adsorption type separation film, the suction should properly be done at a linear flow speed of about 10-50 cm/hour (a value of volumetric flow speed divided by a cross-sectional area). When the filter is a filtration type or arresting type, the flow is one-way so that a control to cause the liquid to pass the filter by ejection or pressurization is required.

The "number of times" refers to the number of ejections performed repetitively on the same liquid being processed or on each of divided liquids. Consider a case, for example, where a certain volume of liquid is divided into predetermined volumes or equally divided volumes and subjected to pressure for a predetermined duration. This allows various volumes of liquid to be pressurized uniformly. In this case, if this process is combined with a process using a pipette tip, the entire process can be automated.

The "tip construction" includes the shape of the tip, and the "construction of the filter-incorporated tip" includes the shape of the nozzle-tipped container, the position of the locked filter, the shape, kind, property, material, pore diameter and pore density of the filter, and the shape of the locking portion. Determining the suction/ejection operation according to the "kind of substance" means that if the substance being handled is smaller in size than proteins, such as a genetic substance of DNA, the amount of liquid being handled is small and needs to be processed at high speed because encounterability generally decreases with the size of substance.

In the nozzle-tipped container having the filter locked therein, the space for accommodating the liquid has a volume of between a few μl and a few hundred μl. In the case of this example, the liquid accommodating portion provided outside the filter-incorporated tip must be able to accommodate a few μl to a few hundred μl of liquid by drawing it by suction into the small-diameter tube through the front nozzle portion of the small-diameter tube.

According to a third aspect, the present invention provides a filtration method, further including: a pressure pattern measuring step to directly or indirectly couple the filter-incorporated tip to the air nozzle, eject the gas from the air nozzle into the into the coupled filter-incorporated tip, and measure a pressure pattern of the filter-incorporated tip before the liquid introducing step or during the pressure application step.

By detecting any deviations from a measured pressure pattern of the normal filter-incorporated tip, it is possible to check for an abnormal construction of the filter-incorporated tip, a liquid leakage, a gas leakage and an abnormal filter. When such an abnormal pressure pattern is detected, a control may be executed which involves, for example, temporarily stopping the pressure application, replacing the filter-incorporated tip with a new one, then resuming the process, or temporarily stopping the process and, after a certain length of time, repeating the same operations.

According to a fourth aspect, the present invention provides a filtration method further including: a preprocessing step to process the subject liquid using a pipette tip or two-or-more-ganged pipette tips fitted to the air nozzle before the liquid introducing step, the air nozzle being capable of performing a suction of gas in addition to the ejection; wherein the liquid introducing step involves introducing the liquid into the filter-incorporated tip using the pipette tip; wherein the coupling step involves removing the pipette tip from the air nozzle and then coupling the filter-incorporated tip or the member and the filter-incorporated tip to the air nozzle.

Here, the "preprocessing step" may include a stirring step and an isolation step. The stirring step repeats the suction/ejection operation using the pipette tip. The isolation step applies a magnetic field from outside to the liquid that suspends magnetic particles covered with a predetermined material as the liquid is sucked and ejected by the pipette tip, thereby separating the magnetic particles.

The whole or part of the wall of the pipette tip may be formed of a conductive member having a predetermined electric resistance.

According to a fifth aspect, the present invention provides a filtration method, wherein the pressure applied through the air nozzle in the pressure application step is constant over time.

If a constant pressure is applied over time, a gas pressure measured above the filter in the filter-incorporated tip changes over time as the liquid or gas passes through the filter. Examples of such measurements are shown in FIG. 10 and FIG. 11.

According to a sixth aspect, the present invention provides a filter-incorporated tip comprising: a nozzle-tipped container having a guide opening portion that can be directly or indirectly coupled to an air nozzle capable of ejecting a gas and a front nozzle portion capable of delivering a liquid by the ejection of the gas from the air nozzle; and a filter locked in the nozzle-tipped container to partition the interior of the nozzle-tipped container into the guide opening portion side and the front nozzle portion side, the filter being adapted to temporarily hold the liquid and isolate a predetermined substance as the liquid passes through the filter, with the nozzle-tipped container coupled to the air nozzle on the guide opening portion side.

According to a seventh aspect, the present invention provides a filter-incorporated tip, wherein the nozzle-tipped container has a large-diameter tube, a small-diameter tube provided below the large-diameter tube and formed narrower than the large-diameter tube, and a transition portion provided between the large diameter tube and the small-diameter tube; wherein the guide opening portion is provided at an upper end of the large-diameter tube; wherein the front nozzle portion is provided at a front end of the small-diameter tube.

Therefore, the "transition portion" has, for example, a step or inclined surface.

The guide tube and the filter locking tube may be formed integral as one piece or formed as separable pieces.

According to an eighth aspect, the present invention provides a filter-incorporated tip, wherein the nozzle-tipped container has a filter locking portion to lock the filter in the nozzle-tipped container so that the liquid introduced into the nozzle-tipped container can come into contact with the filter.

Examples of the "filter locking portion" include a penetrative porous member or a meshed member with penetrating holes that passes a liquid but not the filter and which is provided separate from the nozzle-tipped container; the nozzle-tipped container itself, for example, with its wall deformed or worked; and a combination of the separate member and the nozzle-tipped container with a worked wall. As an example of the filter locking portion that uses the nozzle-tipped container itself, there is a structure in which the tube of the nozzle-tipped container is throttled by an inwardly bulged protrusion that protrudes toward the center of the tube.

The "penetrative porous member" of the filter locking portion does not need to be a filter that arrests a substance by adsorption. However, if the filter to be locked is a thin-film filter, the penetrative porous member may also be able to arrest a substance of a predetermined size in addition to being able prevent the filter from being carried away from the front nozzle portion or guide opening portion. Where the filter locking portion is provided separate from the nozzle-tipped container, it uses a thin-plate or thin-film member with a small thickness in the direction of liquid flow. If the filter to be locked is a thin-film filter, the filter locking portion uses a penetrative porous member with pores of a large diameter that will not slacken the filter. Where the filter locking portion uses the worked nozzle-tipped container, its opening portion is made large only to an extent that can still prevent the thin-film filter from slacking and a block-shaped filter from flowing out therethrough, thereby making it possible to reduce the pressure required for suction/ejection operation.

According to a ninth aspect, the present invention provides a filter-incorporated tip, wherein the filter locking portion has one or more filter support members provided separate from the nozzle-tipped container so that the filter support members can partition the interior of the nozzle-tipped container into the front nozzle portion side and the guide opening portion side.

Here the "filter support member" is formed separate from the nozzle-tipped container. It may be a combination of the member formed separate from the nozzle-tipped container and the nozzle-tipped container with a worked wall. The filter support member has penetrative holes or gaps so sized as to pass a liquid but not the filter. The filter support member is also shaped and sized so as not to slacken the thin-film filter. For example, they may be formed in various shapes, such as wheels, crosses, straight lines, radials and nets. They may also be formed of members or penetrative porous members so disposed as to divide the small-diameter tube into rings.

The filter locking portion that use the nozzle-tipped container itself may have a protrusion bulging toward the center of the tube to throttle the nozzle-tipped container. The filter locking portion may also be connected to the filter.

To prevent the filter from being carried away from the front nozzle portion or from the guide opening portion, the filter support members should preferably be installed at least two locations so that the filter can be held between them from both sides—the front nozzle portion side and the guide opening portion side.

The filter support members may use a penetrative porous member so that they can reliably hold and lock a variety of filters of sizes larger than the pore diameters.

By removably installing the filter support members that are provided separate from the nozzle-tipped container, the filter can be held and locked and taken out easily.

According to a tenth aspect, the present invention provides a filter-incorporated tip, wherein the locking portion has between the guide opening portion and the front nozzle portion a protruding portion protruding inwardly from an inner wall surface of the nozzle-tipped container, an inclined surface or a step; wherein the protruding portion, the inclined surface or the step holds the filter or the filter support members by locking them in the nozzle-tipped container.

In this construction, since the filter locking portion is provided by working or deforming the nozzle-tipped container itself and no separate filter locking portion is used, the filter can reliably be held and locked. Further, by using the nozzle-tipped container, especially the step or inclined surface provided at the transition portion, the filter support members can reliably be locked and held.

According to an eleventh aspect, the present invention provides a filter-incorporated tip, wherein the nozzle-tipped container has a guide tube with the guide opening portion and a filter locking tube provided below and communicating with the guide tube and having the front nozzle portion at a lower end thereof; wherein the filter is provided in the filter locking tube above the front nozzle portion to partition the interior of the filter locking tube into the guide tube side and the front nozzle portion side; wherein the guide tube and the filter locking tube are removably connected with each other.

With this construction, the nozzle-tipped container therefore can be divided into at least two parts such that the guide opening portion and the front nozzle portion are separated.

According to a twelfth aspect, the present invention provides a filter-incorporated tip, wherein the guide tube has a large-diameter tube; wherein the filter locking tube has a small-diameter tube formed narrower than the large-diameter tube and a transition portion provided between the large-diameter tube and the small-diameter tube.

In this case, the filter can be inserted from a divided portion between the large-diameter tube and the transition portion. The large-diameter tube, the transition portion and the small-diameter tube may be formed separable from one another.

According to a thirteenth aspect, the present invention provides a filtration device comprising: an air nozzle head having one or more-ganged air nozzles to perform suction and ejection of a gas; a suction/ejection mechanism to perform the suction/ejection of gas through the air nozzle; one or more filter-incorporated tip directly or indirectly connected or connectable to the air nozzle and having a filter locked therein, the filter being adapted to isolate a target substance as a liquid passes through the filter; a stage having arranged thereon a group of liquid accommodation portions accommodating or capable of accommodating a variety of liquids; a drive means to move the nozzle head relative to the liquid accommodation portions; and a control unit to control a suction or ejection volume to or from the air nozzle, a pressure, a speed, the number of operations, a time or position according to a construction of the air nozzle, a member fitted to the air nozzle or the filter-incorporated tip, according to physical conditions including a kind of substance present in the liquid, a density of the substance, a volume of the liquid and a coordinate position including liquid accommodation position, and according to a content of the process to be performed on the liquid.

Here, the air nozzle is so constructed as to be connectable with a pipette tip as well as the filter-incorporated tip. The stage is preferably provided with the filter-incorporated tips and/or the pipette tips.

According to a fourteenth aspect, the present invention provides a filtration device, wherein the air nozzle has a pressure sensor; wherein the control unit performs control based on a pressure pattern detected by the pressure sensor.

According to a fifteenth aspect, the present invention provides a filtration device, wherein the stage has an evaporation prevention cover comprising a plate and at least two engagement cylinders protruding upward from an upper side of the plate and provided at positions corresponding to the nozzle positions of the nozzle head, the engagement cylinders being adapted to engage with the nozzles and, in the engaged state, be moved by the drive means.

The evaporation prevention cover is preferably dismountable from the air nozzle of the filter-incorporated tip or the pipette tip by a dismounting mechanism.

In the first aspect of the invention, the liquid to be processed is introduced through the guide opening portion into the nozzle-tipped container on the guide opening portion side of the filter locked therein, the filter partitioning the nozzle-tipped container. The filter-incorporated tip, in which the liquid was introduced, is directly or indirectly coupled to the air nozzle. Then, the air nozzle applies a pressure to force the liquid to pass through the filter to isolate a predetermined substance. Thus, if the filter is difficult for the liquid to pass through, this construction enables an object substance in the liquid to be isolated quickly and efficiently.

Since the air nozzle is removably coupled with the filter-incorporated tip, a series of operations including the filtration process by the filter can be automated easily.

This construction allows any desired liquid selected from externally provided liquids to be pressurized, with the filter locked in the nozzle-tipped container. Therefore, by replacing the filtration process with a relative movement between the filter-incorporated tip and the externally provided container and with a suction/ejection control, a series of operations can easily be automated and modified in a variety of ways.

The use of the filter-incorporated tip having a filter securely locked therein and a suction/ejection mechanism having an air nozzle obviates the need for the centrifuge and thus minimize the scale of the device.

With this aspect of the invention, the filtration process and other various processes, such as reaction, washing, temperature control, separation, stirring, pipetting, settling, isolation, elution and extraction, can be executed with simple operations, i.e., the suction or ejection of the liquid with the filter locked in the nozzle-tipped container and the movement of the nozzle-tipped container. It is therefore possible to perform processes efficiently, quickly and easily.

In the second or 13th aspect of the invention, with the filter-incorporated tip directly or indirectly coupled to the air nozzle, the ejection mechanism is activated to control the amount of ejection, the ejection speed, the number of ejections and the position where the ejection operation is performed, according to the construction of the nozzle-tipped container. Thus, by performing a fine control on the amount of gas ejection through the air nozzle, the gas pressure, the ejection speed, the number of ejections and the ejection operation position according to the construction of the nozzle-tipped container, the process of the liquid containing an object biological substance through the filter of the filter-incorporated tip can be performed easily, quickly and efficiently in an automated sequence of operations with high reliability. With these aspects of the invention, a versatility and a range of application can be widened by modifying the content of control and therefore a variety of processes can be dealt with.

With these aspects of the invention, since a fine pressurization control can be executed, a filtration can be performed under an optimal condition for the filter, liquid or object substance. Therefore, depending on the purpose of the process, the performance or efficiency of the isolation, extraction and purification operations can be enhanced.

Further, with these aspects of the invention, by selecting the liquid speed according to the object of the process and the nozzle-tipped container according to the amount of liquid being handled, various processes can be dealt with. That is, a versatility and a wide range of application can be assured.

In the third or 14th aspect of the invention, the filter-incorporated tip is directly or indirectly coupled to the air nozzle which then ejects a gas for measurement of the pressure pattern on the filter. From the pressure pattern, data relating to a property of the filter is acquired. This filter property data is used to check for a possible filter failure, a failure of the nozzle-tipped container and a failed air-tightness between the coupled air nozzle and filter-incorporated tip. The filter property data is also used for control. The use of the filter property data therefore allows for a highly reliable execution of the process.

In the fourth aspect of the invention, the liquid is processed using a pipette tip coupled to the air nozzle before the liquid introducing step. The process can therefore be performed efficiently.

In the fifth aspect of the invention, a constant pressure is applied over time to stabilize the flow of liquid passing through the filter, assuring a smooth, quick passage of the liquid through the filter and therefore a quick and efficient execution of the process.

In the sixth aspect of the invention, the filter-incorporated tip can be directly or indirectly coupled to the air nozzle through the guide opening portion, the air nozzle being adapted to eject at least a gas. Therefore by introducing the liquid to be processed onto the upper side of the filter and applying a pressure to the liquid, it is possible to isolate an object substance in the liquid quickly and efficiently even if the filter is difficult for the liquid to pass through.

Since a finely tuned pressure application control can be performed by controlling the air nozzle, the filtration process can be executed under an optical condition for the filter, liquid or object substance. Thus, the isolation, extraction and purification performance or efficiency can be enhanced according to the object of the process.

Removably coupling the filter-incorporated tip to the air nozzle allows a series of operations, including the filtration process, to be automated easily.

Any desired liquid chosen from among externally provided liquids can be introduced into the nozzle-tipped container having a filter locked therein, and then pressurized. Thus, by replacing the filtration process with the relative motion between the filter-incorporated tip and the externally provided container and with the suction/ejection control, not only can a process automation be achieved but versatility and the range of application of this method can also be widened easily.

The use of the filter-incorporated tip and the suction/ejection mechanism having an air nozzle obviates the need for the centrifuge and therefore can minimize the size of the device.

With this aspect of the invention, the filtration process and other various processes, such as reaction, washing, temperature control, separation, stirring, pipetting, settling, isolation, elution and extraction, can be executed with simple operations, i.e., the suction or ejection of the liquid with the filter locked in the nozzle-tipped container and the movement of the nozzle-tipped container. It is therefore possible to perform processes efficiently, quickly and easily.

Further, with these aspects of the invention, by selecting the liquid speed according to the object of the process and the nozzle-tipped container according to the amount of liquid being handled, various processes can be dealt with. That is, a versatility and a wide range of application can be assured.

In the seventh aspect of the invention, the nozzle-tipped container is provided with a large-diameter tube and a small-diameter tube formed narrower than the large-diameter tube. Since the pressure application process can be performed with a container with a small-diameter opening placed below the nozzle-tipped container, it is possible to handle a wide range of containers of various volumes and a variety of volumes of liquid. This means that the method of this invention has a versatility. Further, using the transition portion between the large-diameter tube and the small-diameter tube, the filter and the filter support members can be reliably locked and held.

In the eighth aspect of the invention, since the filter is locked in the nozzle-tipped container by the locking portion, a variety of kinds of filters can be used by employing the matching locking portions. Thus versatility and the range of application can be widened.

In the ninth aspect of the invention, the filter support members are provided separate from the nozzle-tipped container. Thus, by installing the filter support members in the nozzle-tipped container, the filter can easily be locked. Further, by removably installing the filter support members, the tip member can be reused and the substance separated by the filter can be directly extracted or collected.

In the tenth aspect of the invention, the filter locking portion is provided in the form of an inwardly protruding portion bulging from the inner wall surface of the nozzle-tipped container, in the form of an inclined surface or in the form of a step. This construction reduces the parts count and therefore the manufacturing cost and makes it possible to reliably lock the filter.

The filter or filter support members are locked and securely held by the protruding portion, the inclined surface or the step. Therefore, the locking of the filter in the nozzle-tipped container is secure and reliable.

Particularly by using the step and the inclined surface of the transition portion ranging from the small-diameter tube to the large-diameter tube of the nozzle-tipped container, the filter or the filter support members are held in the nozzle-tipped container. This construction assures an easy and reliable locking of the filter without having to work the nozzle-tipped container.

In the 11th or 12th aspect of the invention, the nozzle-tipped container is made divisible in at least two parts so that the guide opening portion and the front nozzle portion can be separated from each other. This construction renders the locking of the filter easy and allows for repetitive use of the nozzle-tipped container by replacing the filter.

In the 15th aspect of the invention, the evaporation prevention cover can be moved along with the air nozzle so that a container or well, in which incubation is to be performed, can be closed. Thus, in the process of incubation, the evaporation prevention for the liquid can easily be automatically accomplished. Further, the evaporation prevention cover still attached to the air nozzle may be pressed against the container or well along with the air nozzle.

DESCRIPTION OF THE PREFERRED EMBODIMENTS

Figure 1:
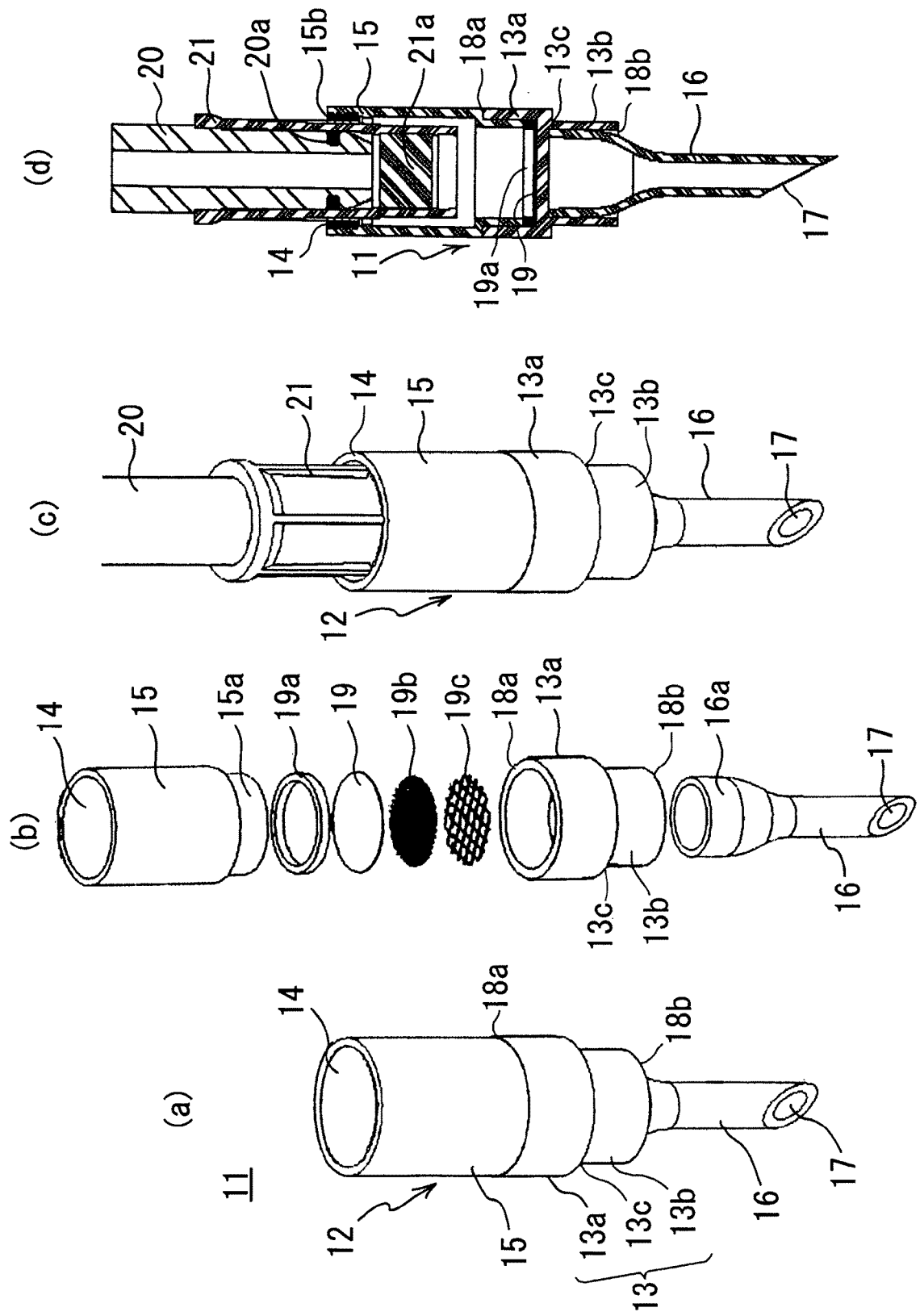
FIG. 1 shows a filter-incorporated tip according to a first embodiment of this invention.

Now, preferred embodiments of this invention will be described by referring to the accompanying drawings. The descriptions that follow, unless otherwise specifically stated, must not be construed as limiting the present invention in any way.

FIG. 1(a) shows an external view of a filter-incorporated tip according to the first embodiment of this invention.

The filter-incorporated tip 11 has a nozzle-tipped container 12 incorporating a thin-film filter 19 to be described later. The nozzle-tipped container 12 comprises a guide tube 15 with a large diameter of a few millimeters to several tens of millimeters, preferably a few millimeters to ten-odd millimeters, a narrow tube 16 formed narrower than the guide tube 15, and a transition portion 13 provided between the guide tube 15 and the narrow tube 16. Here, the narrow tube 16 and the transition portion 13 correspond to the filter locking tube. These components are separable at an opening portion 18a between the guide tube 15 and the transition portion 13 and also at an opening portion 18b between the transition portion 13 and the narrow tube 16. On the upper side of the guide tube 15 is provided a guide opening portion 14. At a lower end of the narrow tube 16 is provided a front nozzle portion 17 that has an end face inclined with respect to an axis of the nozzle-tipped container 12. The transition portion 13 has an upper portion 13a with the same outer diameter as that of the guide tube 15 and a lower portion 13b with an outer diameter smaller than that of the guide tube 15 but larger than that of the narrow tube 16. The transition portion 13 also has a step portion 13c at an almost central part thereof.

The nozzle-tipped container 12 is formed of, for example, polyethylene and polypropylene to allow its interior to be optically observed from outside. The container may have a capacity of, say, several microliters to several hundred microliters, preferably a few tens of microliters.

FIG. 1(b) is an exploded perspective view of the filter-incorporated tip 11. The guide tube 15 of the filter-incorporated tip 11 has formed at a lower end thereof a downwardly protruding engagement portion 15a that is slightly narrower than the outer diameter of the body of the guide tube 15 and fits into the opening portion 18a of the upper portion 13a of the transition portion 13. When the engagement portion 15a is fitted in the transition portion 13, the front end of the engagement portion 15a is spaced apart from the inner upper end of the step portion 13c to form an annular groove between them. In this annular groove parts such as shown in FIG. 1(b) are installed in layers and firmly held there. These parts are a rubber O-ring 19a elastically biasing downwardly filters stacked below, the thin-film filter 19 with a predetermined mesh size, a meshed thin plate 19b having a mesh size slightly larger than that of the thin-film filter 19 and adapted mainly to support the thin-film filter 19 tightly, and a meshed thin plate 19c provided under the meshed thin plate 19b and having a larger mesh size than that of the meshed thin plate 19b to prevent a clogging of the thin-film filter 19.

The thin-film filter 19 and the meshed thin plates 19b, 19c are installed so as to separate the guide opening portion 14 and the front nozzle portion 17. The meshed thin plates 19b, 19c corresponds to the filter support member separate from the nozzle-tipped container 12. The meshed thin plates 19b, 19c, along with the step portion 13c, correspond to the filter locking portion. The thin-film filter 19 is, for example, an ultrafiltration membrane formed of regenerated cellulose. The meshed thin plate 19b is made of stainless steel with a pore diameter of, for example, about 50 µm. The meshed thin plate 19c is made of stainless steel with a pore density of, for example, 40 m/s.

As shown in FIG. 1(b), the narrow tube 16 has an engagement portion 16a formed at the top thereof that is fitted into the opening portion 18b of the lower portion 13b of the transition portion 13.

As shown in a perspective view and a cross-sectional view of FIG. 1(c), 1(d), the guide opening portion 14 of the guide tube 15 is removably attached with a cylindrical adapter 21 to prevent cross-contamination. The cylindrical adapter 21 in turn can removably be fitted over an air nozzle 20 that draws in and ejects a gas. Further, the front nozzle portion 17 at the front end of the narrow tube 16 can draw in and eject a liquid by the suction and ejection of air through the air nozzle 20.

Inside the cylindrical adapter 21 an air filter 21a is installed to separate end opening portions of the cylindrical adapter 21 from each other. The air nozzle 20 is coupled to the adapter so that its front end is close to or in contact with the upper end of the air filter 21a or the member such as the meshed thin plate on which the air filter 21a is mounted. Near the front end of the air nozzle 20 an O-ring 20a is installed to prevent a gas leakage.

The cylindrical adapter 21 is elastically biased to fit into the guide opening portion 14 by a rubber O-ring 15b installed near an upper opening of the guide opening portion 14.

Figure 2:
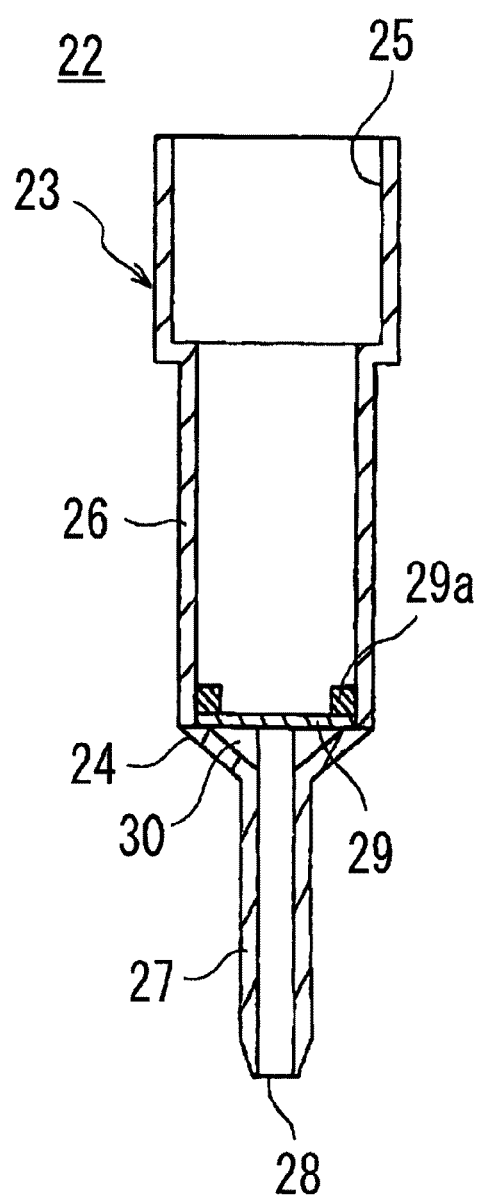
FIG. 2 shows a filter-incorporated tip according to a second embodiment of this invention.

FIG. 2 shows a filter-incorporated tip 22 according to a second embodiment of this invention.

The filter-incorporated tip 22 has a nozzle-tipped container 23 and a thin-plate filter 29 described later which is locked inside.

The nozzle-tipped container 23 has a large-diameter tube 26, a small-diameter tube 27 communicating with and formed narrower than the large-diameter tube 26, and a transition portion 24 provided between the large-diameter tube 26 and the small-diameter tube 27. In this embodiment, unlike the first embodiment, the large-diameter tube 26, the transition portion 24 and the small-diameter tube 27 are not separable. On the top of the large-diameter tube 26 is provided a guide opening portion 25. At a lower end of the small-diameter tube 27 is provided a front nozzle portion 28. The transition portion 24 is generally conical, when viewed from outside, and installed coaxial with the small-diameter tube 27. It has a plurality of right triangular support plates 30 radially extending from a position corresponding to the inner diameter of the small-diameter tube 27 to the inner wall of the transition portion 24. The upper edges of these support plates 30 are aligned horizontal and extend perpendicular to the axis of the filter-incorporated tip 22. On these edges is placed the thin-plate filter 29. The thin-plate filter 29 is elastically biased from above by a rubber O-ring 29a.

The nozzle-tipped container 23 is formed of, for example, polyethylene and polypropylene to allow the interior state to be optically observed from outside. The small-diameter tube 27 has a capacity of, for instance, a few microliters to a few hundred microliters.

The thin-plate filter 29 separates the guide opening portion 25 and the front nozzle portion 28 from each other. The rubber O-ring 29a corresponds to the filter support member provided separate from the nozzle-tipped container 23. The support plates 30 correspond to the protruding portion that protrudes inwardly from the inner wall surface of the nozzle-tipped container 23 between the guide opening portion 25 and the front nozzle portion 28.

The guide opening portion 25 can be removably coupled with an air nozzle (not shown) that draws in and ejects a gas or with an adapter (not shown) that is removably fitted to the air nozzle. The front nozzle portion 28 at the front end of the small-diameter tube 27 can draw in or eject a liquid by the suction and ejection of air by the air nozzle.

Figure 3:
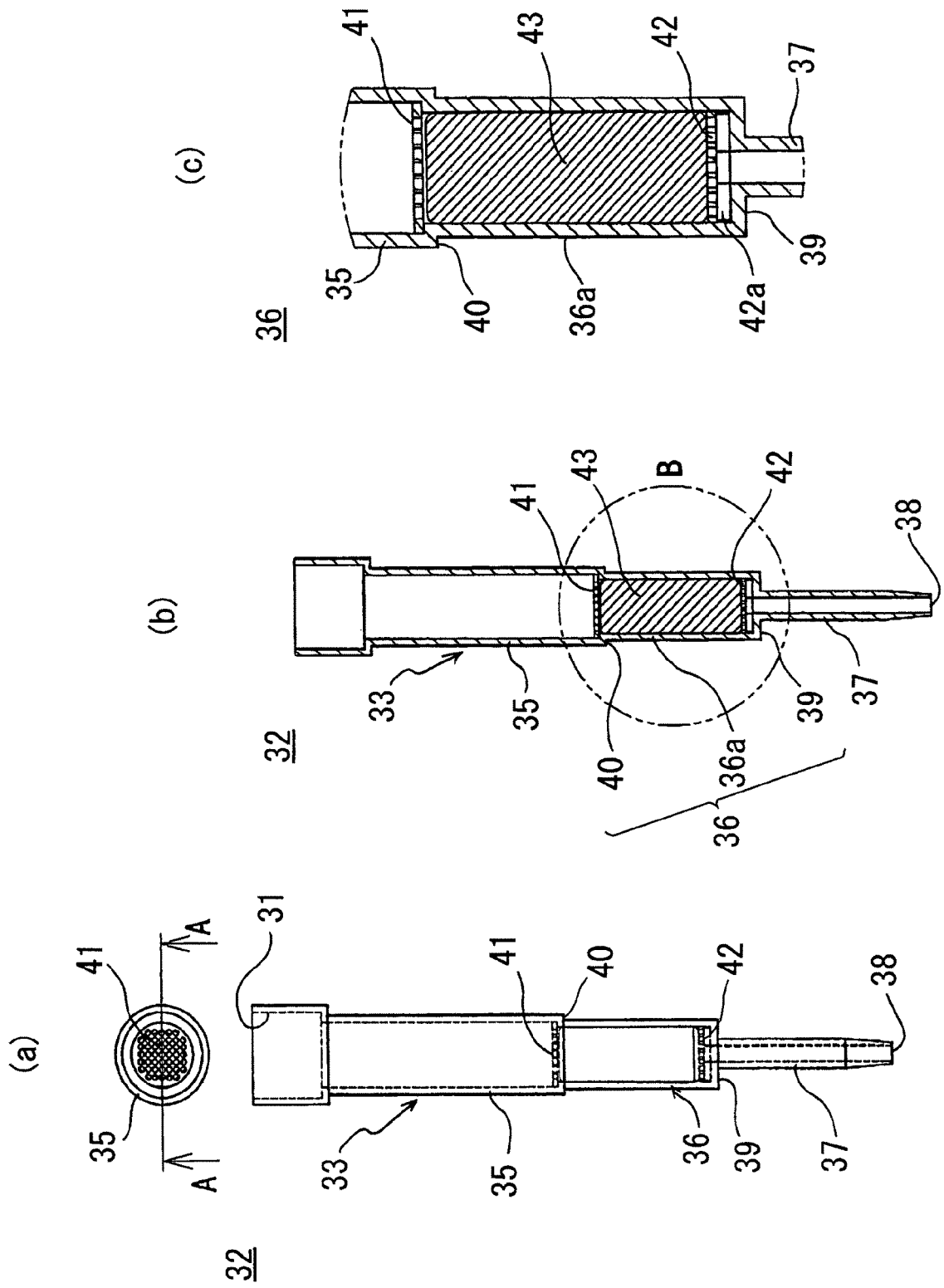
FIG. 3 shows a filter-incorporated tip according to a third embodiment of this invention.

FIG. 3 shows a filter-incorporated tip 32 according to a third embodiment.

As shown in FIG. 3(a) and FIG. 3(b) which is a cross-sectional view taken along the line AA of FIG. 3(a), the filter-incorporated tip 32 has a cylindrical, permeable, porous block filter 43 held in a nozzle-tipped container 33.

The nozzle-tipped container 33 has a roughly cylindrical large-diameter tube 35, a small-diameter tube 37 communicating with and formed narrower than the large-diameter tube 35, a filter accommodating tube 36a capable of accommodating the block filter 43 with a diameter intermediate between those of the large-diameter tube 35 and the small-diameter tube 37, and a transition portion 36 having a step 40 formed between it and the large-diameter tube 35 and a step 39 formed between it and the small-diameter tube 37. The inner diameter and depth of the filter accommodating tube 36a of the transition portion 36 are almost equal to the outer diameter and height of the block filter 43 so that the filter accommodating tube 36a can accommodate the block filter 43 with almost no gap between them. Permeable, porous thin plates 41, 42 are locked and held at the steps 39, 40 of the transition portion 36, respectively, to separate a guide opening portion 34 and a front nozzle portion 38. The permeable, porous thin plates 41, 42 correspond to the filter support member.

At the upper end of the large-diameter tube 35 there is provided a cylindrical guide opening portion 34 that is removably coupled to an air nozzle, not shown, for gas suction and delivery or to a tip or adapter removably attached to the air nozzle. The small-diameter tube 37 has formed at its front end a front nozzle portion 38 through which a liquid can be drawn in or out by the suction and delivery of gas by the air nozzle.

FIG. 3(b) shows the block filter 43 installed in the filter accommodating tube 36a of the transition portion 36. As shown in FIG. 3(c), an enlarged view of part B, the block filter 43 is enclosed by the permeable, porous thin plate 41 and the permeable, porous thin plate 42 on its upper and lower sides, respectively. The filter accommodating tube 36a is cylindrical and coaxial with the small-diameter tube 37. In the filter accommodating tube 36a, a plurality of rectangular ribs 42a are radially arranged on the step 39 and extend from a position corresponding to the inner diameter of the small-diameter tube 37 to the inner wall of the filter accommodating tube 36a. These rectangular ribs 42a support the permeable, porous thin plate 42, thus preventing the holes of the permeable, porous thin plate 42 from being clogged and securely holding it at the step 39. Here, the permeable, porous thin plates 41, 42 constituting the filter support member, the steps 39, 40 and the ribs 42a combine to form the filter locking portion. The filter accommodating tube 36a is coated on its outer wall with a conductive thin film 36b. The filter accommodating tube 36a thus can be temperature-controlled by applying an electric current to the conductive thin film 36b through electrodes.

Figure 4:
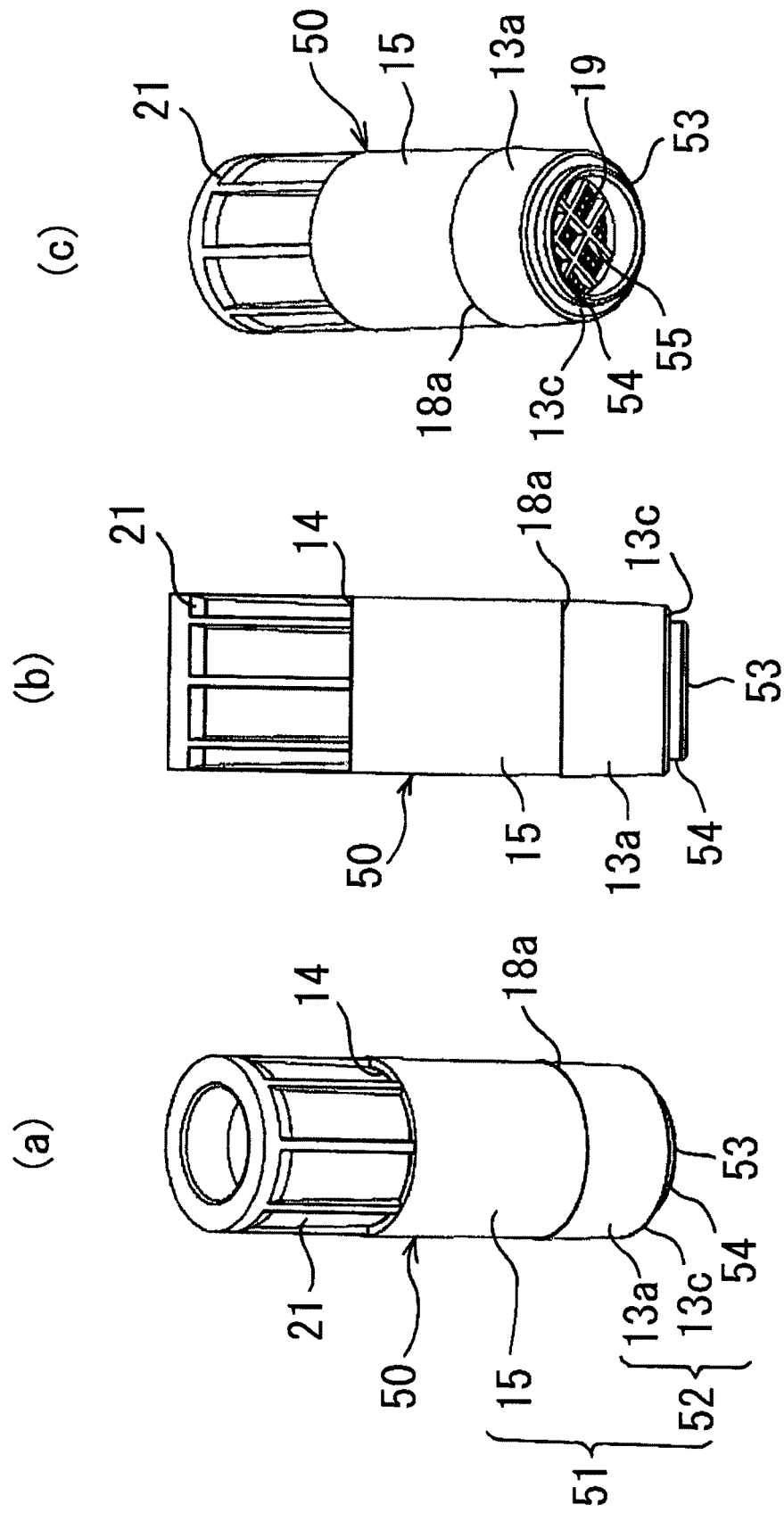
FIG. 4 shows a filter-incorporated tip according to a fourth embodiment of this invention.

FIG. 4 shows a filter-incorporated tip 50 attached with the cylindrical adapter 21 according to a fourth embodiment of this invention.

Components with the same reference numerals as those in FIG. 1 represent identical components and their explanations are omitted. The filter-incorporated tip 50 has a nozzle-tipped container 51 with the built-in thin-film filter 19. The nozzle-tipped container 51 has a guide tube 15 and a filter locking tube 52 communicating with the guide tube 15. The filter locking tube 52 comprises the upper portion 13a of the transition portion 13; a step 13c; a cylindrical short tube 54 having an outer diameter slightly smaller than the outer diameter of the guide tube 15 and protruding downwardly from the step portion 13c of the transition portion 13; and a front nozzle portion 53 at the lower end of the short tube 54. On the lower side of the thin-film filter 19 is installed a lattice-shaped filter locking portion 55 that separates the front nozzle portion 53 and the opening portion 18a of the filter locking tube 52 and supports the thin-film filter 19 from below.

The filter-incorporated tip 50, when compared with the filter-incorporated tips 11, 22, 32 of the preceding embodiments, has a larger inner diameter of the front nozzle portion 53 and a shorter distance from the thin-film filter 19 to the front nozzle portion. So, even if a highly viscous liquid is used, the filter-incorporated tip 50 can prevent the liquid from adhering to the inner wall of a flow path running from the outlet side of the filter to the front nozzle portion, thus allowing for quick and easy delivery of the liquid.

Figure 5:
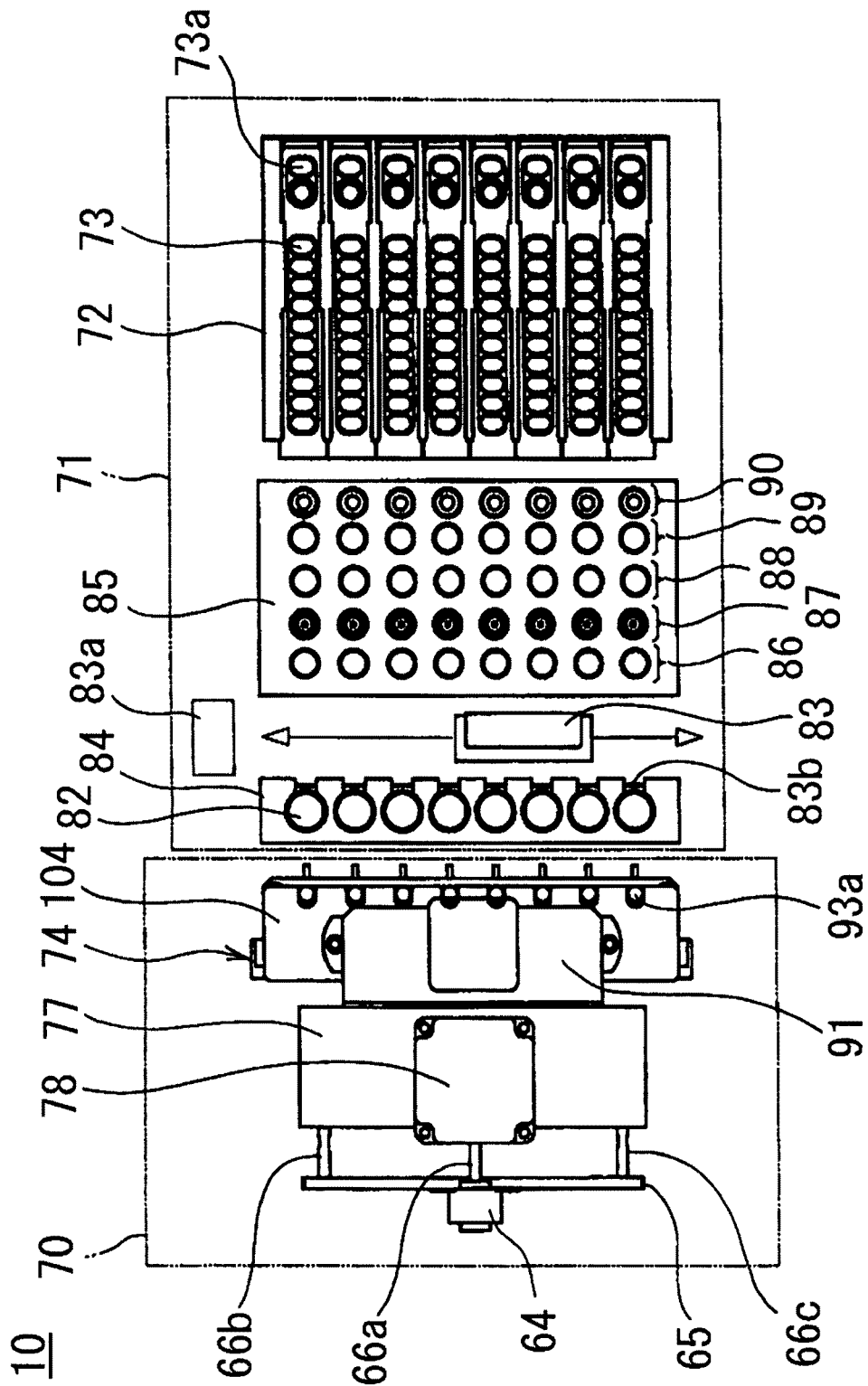
FIG. 5 shows a filtration device according to a fifth embodiment of this invention.

Next, by referring to FIG. 5, a filtration device 10 according to a fifth embodiment of this invention will be explained. FIG. 5 is an overall schematic plan view showing the filtration device 10.

The filtration device 10 has a gas suction/ejection mechanism, which comprises a filter-incorporated tip processing device 70 and a filtration area 71. The filter-incorporated tip processing device 70 has a plurality of air nozzles each of which is coupled to the filter-incorporated tip 11 or filter-incorporated tip 50 to perform an ejection operation on the filter-incorporated tip 11 or a suction/ejection operation on the filter-incorporated tip 50. The filtration area 71 is an area in which solutions containing a variety of samples and reagents are introduced into the filter-incorporated tips 11; in which a gas is ejected into the filter-incorporated tips 11 to cause liquids to pass through the filter; in which products obtained by the filtration are accommodated; in which operations, such as pipetting, stirring, washing, extraction, transfer and reaction, are performed to prepare solutions to be introduced; or in which a variety of reagents, mixed liquids, solutions, reactive liquid or samples are accommodated.

Figure 6:
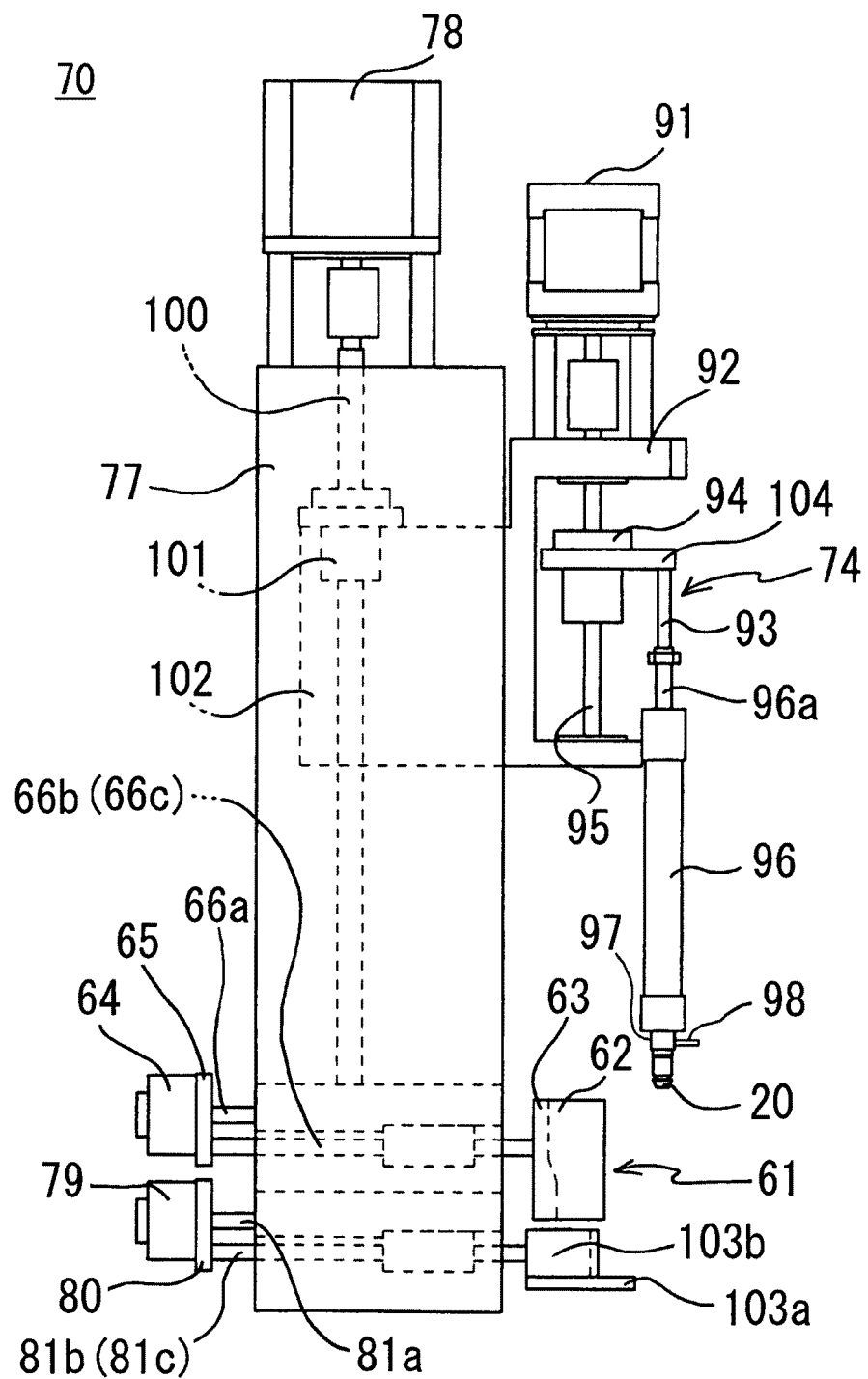
FIG. 6 shows a filter-incorporated tip processing device according to a fifth embodiment of this invention.

The filter-incorporated tip processing device 70 shown in FIG. 5 and FIG. 6 has a nozzle head 74 which has a plurality of air nozzles 20 (eight of them in this example) arranged in a column direction (a vertical direction in the figure) at eight locations 93a in FIG. 5. The nozzle head 74 undergoes the suction and ejection for all air nozzles at one time.

As shown in FIG. 6, the suction/ejection mechanism comprises a connecting portion 97 that connects to a cylinder 96 provided slightly above each air nozzle 20 and has a flow path 98 to introduce a gas into a pressure sensor (not shown) for detecting a pressure in the air nozzle 20; a cylinder 96 that connects to the air nozzle 20 through the connecting portion 97; a plunger 96a that slides inside the cylinder 96; and a rod 93 provided for each of the eight-ganged air nozzles 20 that drives the plunger 96a. The eight rods 93 are mounted to a drive plate 104 designed to move all the rods at one time in such a manner that eight-ganged end portions 93a of the rods 93 radially protruding and having a larger radius than that of each rod 93 engage the eight-ganged notches formed at an edge of the drive plate 104. The nozzle head 74 is moved in a row direction (horizontal or lateral direction in the figure).

As shown in FIG. 6, the drive plate 104 is connected to a nut portion 94 that engages a ball screw 95. Each of the rods 93 is urged downward at all times by a spring installed in the cylinder 96. So, the rod 93, when it moves up, is driven upward by the nut portion 94. When it moves down, the rod 93 is driven down by the force of the spring, not by the nut portion 94. Each of the ball screws 95 is rotated by a motor 91 mounted on a support member 92 U-shaped in cross section to move the drive plate 104 and the eight rods 93 at once.

Since the eight-ganged air nozzles 20 are mounted to the nozzle head 74, they undergo the suction and ejection operations at one time. In a vertical drive mechanism, too, all air nozzles 20 are moved at once horizontally (laterally in FIG. 5) or in a row direction (X-axis direction).

In FIG. 6, a case 77 accommodates a ball screw 100, a nut portion 101 engaging the ball screw 100, and a support member 102 having at one end thereof the support member 92 mounted to the nut portion 101. On the case 77 is installed a motor 78 that rotates the ball screw 100. The vertical drive mechanism constructed of these components can drive the air nozzles 20 vertically at once.

In a lower part of the case 77 is provided a temperature vertical means 61. The temperature vertical means 61 comprises heating plates 63 that are formed along a column direction to have such a height and width as to be able to come close to or in contact with the eight pipette tips fitted to the eight-ganged air nozzles and which incorporates a heater; and 10 heating walls 62 each incorporating a heater and mounted to the heating plates 63 so that they hold the individual tips from both sides. These heating plate 63 is preferably shaped to conform to the shapes of the tips to be temperature-controlled. The heating plates 63 and the heating walls 62 correspond to the temperature vertical member.

The temperature vertical means 61 also has a motor 64 to enable the heating walls to come close to or in contact with the tips fitted to the air nozzles 20 of the nozzle head 74 to heat the tips; a ball screw 66a driven by the motor 64; a traveling support plate 65 having a nut portion that engages the ball screw 66a; and moving rods 66b, 66c capable of coupling to the traveling support plate 65 to travel in a lateral direction in the figure and also capable of coupling to the heating walls 62 and the heating plate 63.

Below the temperature vertical means 61 there are provided a comb-shaped claw 103a with a semicircular recess conforming to the outer surface of the air nozzle 20 and eight magnets 103b; a motor 79 for moving the claw 103a and the magnets 103b in the lateral direction in the figure to remove the filter-incorporated tip 11 attached to the air nozzle 20 or to apply a magnetic field to it; a ball screw 81a driven by the motor 79; a traveling support plate 80 movable in the lateral direction in the figure and having a nut portion engaging the ball screw 81a; and a moving rod 81b (81c) mounted to the traveling support plate 80.

The filter-incorporated tip processing device 70 is suspended from above so that it can be moved by an X-axis (row direction) drive mechanism using a linear motion mechanism not shown to cover the entire area or some necessary areas of the filtration device 10.

Now returning to FIG. 5, in the filtration area 71 there are provided a cartridge container 84 having 8-ganged target substance accommodation wells 82 for receiving a solution containing the target substance; a matrixlike container 85 having 5 columns times 8 rows of wells; and eight cartridge containers 72 each having pre-packable wells 73 for accommodating various reagents and substances necessary for the execution of the filtration or for accommodating filtrated materials. Designated 73a in the cartridge containers 72 are incubator wells provided with a heat block. The 5 columns times 8 rows of wells in the matrixlike container 85 are comprised of well columns 86, 88, 89 designed to accommodate products described later and in or over which the front nozzle portions 17 of the filter-incorporated tips 11 are disposed and pressurized; a filter-incorporated tip accommodation column 87 for accommodating the filter-incorporated tips 11; and a pipette tip accommodation column 90 for accommodating the pipette tips.

The target substance accommodation wells 82 are each attached with a barcode 83b indicating information about the target substance. The barcode 83b is scanned by a barcode reading portion 83 as it travels in the column direction. Designated 83a is a drive mechanism for driving the barcode reading portion 83.

Though not shown, an information processing device to control the filtration device 10 is provided which has an input device for entering a user command and data, a CPU for executing various computation operations, a display device, a variety of memories, a transmission means, etc. The information processing device issues instructions to and receives signals from the suction/ejection mechanism, the pressure sensor, the drive mechanism and devices inside a matrix path transport means in the filter-incorporated tip processing device 70. The information processing device has a control unit that controls the air nozzle suction/ejection volume, pressure, speed, the number of operations, time or position according to physical conditions—the structures of the air nozzles and of members fitted to the air nozzles or filter-incorporated tips, the kind and concentration of substance present in a liquid, liquid volume, temperature of liquid or filter, or coordinate positions including liquid accommodation positions—and according to details of process to be executed.

Figure 7:
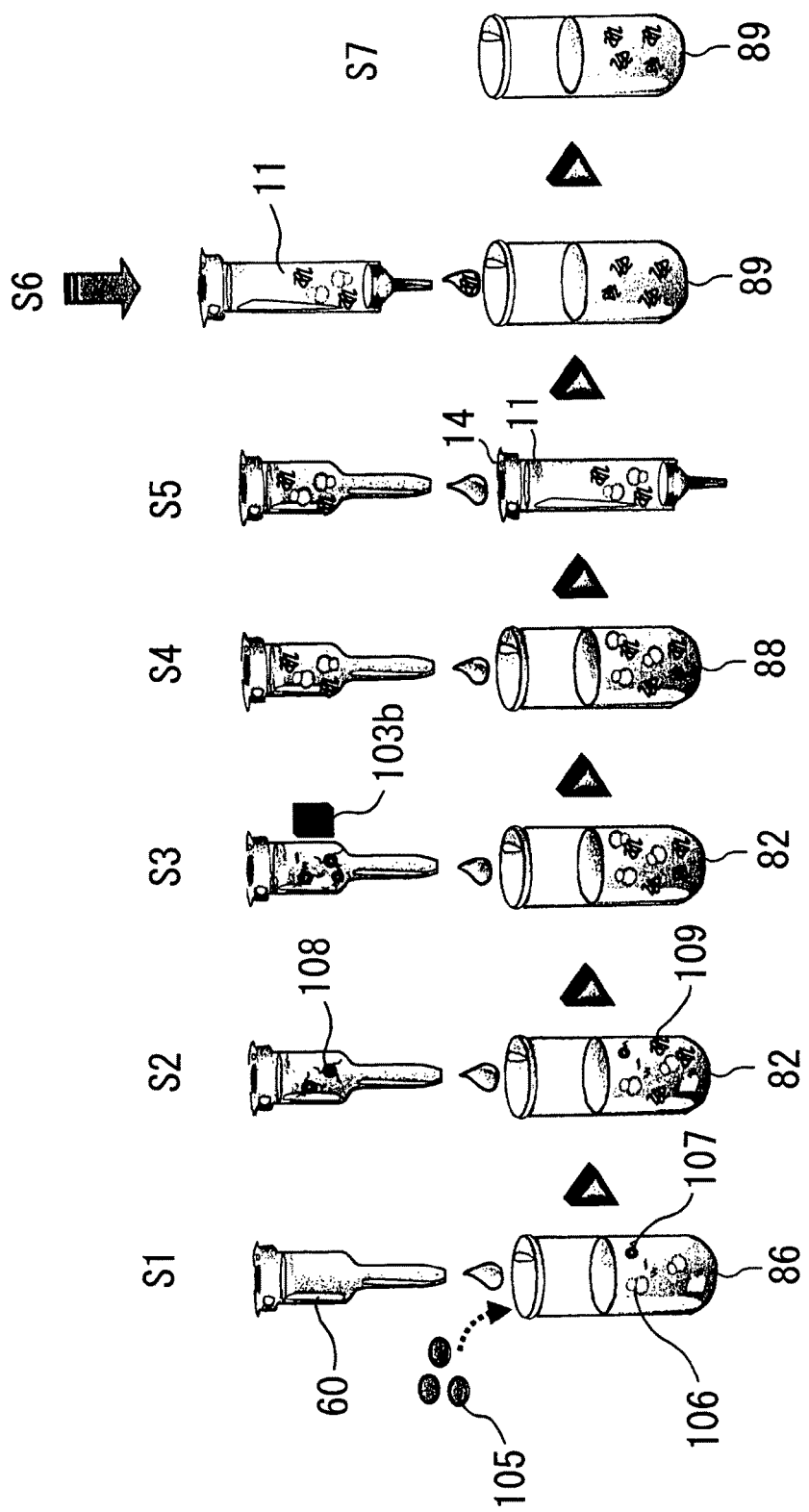
FIG. 7 shows a flow of filtration according to a sixth embodiment of this invention.

Referring to FIG. 7, a process, according to a sixth embodiment, of purifying a target synthesized protein by using the filter-incorporated tip 11 of the first embodiment will be explained.

Here, for the meshed thin plate 19b as the filter support member of the filter-incorporated tip 11, a SUS-316 53 mesh is used. For the meshed thin plate 19c, SUS-304 40 m/s will be used. For the thin-film filter 19 of the filter-incorporated tip 11, an ultrafiltration membrane is used. In this process, as a means for forcing a liquid of interest to easily pass through the thin-film filter 19, three methods were tested under the same condition and compared. The three methods tested are [A] manual pressurization, [B] pressurization at a constant pressure and [C] application of centrifugal force by a centrifuge. The test involves processing eight samples simultaneously by using the filtration device 10 with 8-ganged nozzles and applying the filtration force or pressure to three of the samples.

Before starting the process, the filter-incorporated tips 11 are attached to the air nozzles 20 through the adapters 21 and a gas is ejected into the filter-incorporated tips 11 by the suction/ejection mechanism to introduce the gas through the flow path 98 to the pressure sensor to measure the pressure pattern of the tips. By analyzing the measured pressure pattern, a check is made of the thin-film filter 19 in each filter-incorporated tip 11 for any problem, or the pressure pattern is stored in memory.

At step S1, a reaction solution is made beforehand. To this end, the nozzle head 74 of the filter-incorporated tip processing device 70 in the filtration device 10 is moved by the X-axis drive mechanism not shown to the position of the eight pipette tips 60 accommodated in the pipette tip accommodation column 90. Then, the motor 78 for the vertical drive mechanism is started to lower all of the air nozzles 20 until they are fitted into the openings of the pipette tips 60.

Next, the nozzle head 74 is moved up by the vertical drive mechanism and horizontally moved by the X-axis drive mechanism to a predetermined position. Then, a control is performed to pipette reagents accommodated in the wells of the 8-ganged cartridge containers 72 into the target substance accommodation wells 82 provided in the filtration area 71 to mix them. That is, the target protein is made as follows. 2.5 microliters of a positive control (DHFR) solution containing 0.5 μg of template DNA for synthesizing DHFR (dihydrofolate reductase), 25 μl of Puresystem Sol. A (registered trademark), 10 μl of Puresystem Sol. B (registered trade mark) and 12.5 μl of nuclease free water are sucked into the suction/ejection mechanism made up of the cylinder 96, plunger 96a and rod 93 and then transferred and ejected into the target substance accommodation wells 82 where they are mixed to produce a total of 50 μl of a solution.

The liquids of the Puresystem contain protein factors necessary for transcription, translation and energy regeneration which, after being prepared and generated separately, was reconstructed. That is, they are initiation factor, elongation factor, termination factor, ribosome recycling factor and aminoacyl-tRNA synthetase conforming to 20 different kinds of amino acids. Further, constituent proteins other than ribosome proteins are all adjusted with His-Tag attached to the N-terminal or C-terminal.

In that case, the target substance accommodation wells 82 are kept cool as by getting ice close to them. As a result, a reaction solution containing template DNA 105, ribosome 106 and His-tagged factor 107 is produced in the target substance accommodation wells 82, as shown in FIG. 7. The reaction solution is then sucked in and the nozzle head 74 is moved to the well column 86, that is kept at a constant temperature of 37° C. Then the reaction solution is ejected into the well column 86 and left standing for one hour for synthesis of the target protein.

At step S2, the reaction solution is sucked in from the well column 86, the nozzle head 74 is moved, and the reaction solution is again ejected into the target substance accommodation wells 82 which are again brought close to ice for cooling. In this state, 10 μl of a solution suspending magnetic particles 108 (His-tagged beads: Toyobo) covered with metal affinity resin is sucked in from the wells 73 and then ejected out into the target substance accommodation wells 82 where the liquids are mixed and stirred. For mixing, a suction/ejection operation is repeated at a predetermined speed (for example, a few tens of microliters/second) for about 15 minutes.

At step 3, with the wells cooled as described above, the magnets 103b of the filter-incorporated tip processing device 70 are brought close, from outside, to the pipette tips 60 mounted to the nozzle head 74 to subject them to a magnetic field. Under the influence of the magnetic field, the suction/ejection operation is performed at a predetermined speed (e.g., a few tens of microliters/second) to cause the magnetic particles 108 to adhere to the inner walls of the pipette tips for isolation (B/F isolation).

Since the magnetic particles 108 are bound with the His-tagged factors 107, the B/F isolation of the magnetic particles results in proteins other than the synthesized target protein 109 being eliminated.

At step 4, 50 μl of the top clear layer in the target substance accommodation wells 82 is sucked into the pipette tips 60. (Three products or subjects are prepared: a product or subject 1A for which a method that manually applies a pressure is used; a product or subject 1B for which a method that performs a fully automated pressurization is used; and a product or subject 1C for which a method that applies a centrifugal force instead of pressure is used). The nozzle head 74 is moved to the well column 88, into which the 50 μl of the top clear layer is ejected and to which 50 μl of the nuclease free water is added, making the total volume in the well column 88 amount to 100 μl.

At step S5, the solution is sucked into the pipette tips 60 and then ejected out into the guide opening portion 14 of the filter-incorporated tips 11 accommodated in the filter-incorporated tip accommodation column 87. Now, the reaction solution is accommodated in the large-diameter tube of the filter-incorporated tip 11.

At step S6, the pipette tips 60 are forced down by the comb-shaped claw 103a and the vertical drive mechanism for disconnection from the air nozzles 20 of the nozzle head 74. After this, the air nozzles 20 are inserted into the guide opening portions 14 of the filter-incorporated tips 11 through the cylindrical adapters 21 by using the vertical drive mechanism, thus fitting the filter-incorporated tips 11 over the air nozzles 20. Next, with the filter-incorporated tips 11 attached to the air nozzles 20, the nozzle head 74 is moved to the well column 89 of FIG. 5, into which the front nozzle portion 17 of the narrow tube 16 of each filter-incorporated tip 11 is inserted. In this state, the suction/ejection mechanism of the filter-incorporated tip processing device 70 is activated to eject a gas to pressurize, from above, the reaction solution in the guide tube 15, thereby forcing the reaction solution to pass through the thin-film filter 19 or ultrafiltration membrane. This step is carried out in three different ways. That is, a subject [A] undergoes a process that manually applies a non-constant pressure to the subject; a subject [B] undergoes a process that automatically applies a constant pressure to the subject; and a subject [C] undergoes a (conventional) process that applies a centrifugal force instead of pressure to the subject. At step S7, a solution containing a synthesized target protein 109 removed of ribosome can be produced in the well column 89. (Three products or subjects are prepared: a product or subject 2A for which a method that manually applies a pressure is used; a product or subject 2B for which a method that performs a fully automated pressurization is used; and a product or subject 2C for which a method that applies a centrifugal force instead of pressure is used).

Figure 8:
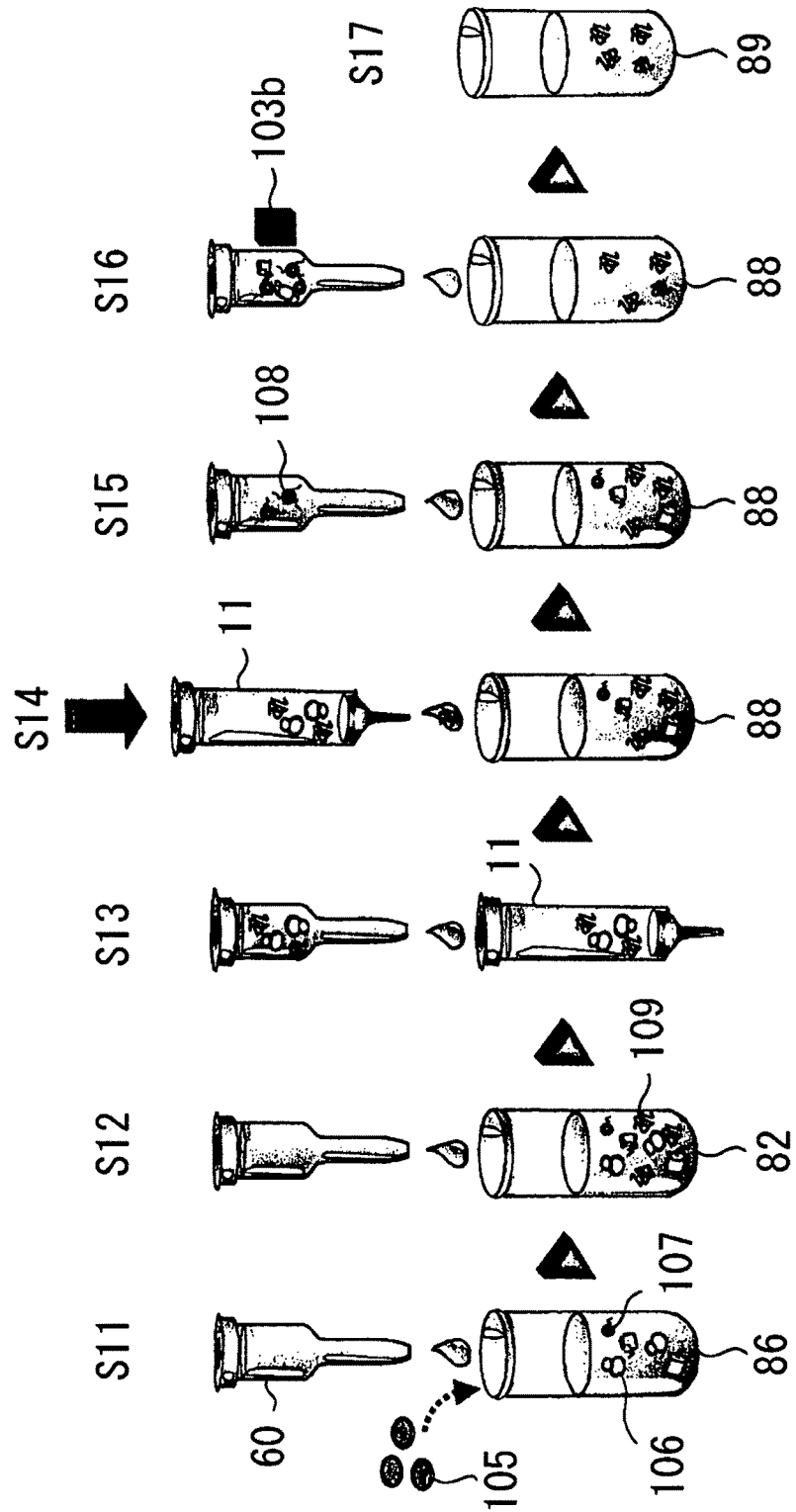
FIG. 8 shows a flow of filtration according to a seventh embodiment of this invention.

Referring to FIG. 8, a process, according to a seventh embodiment, of purifying a synthesized target protein by using the filter-incorporated tip 11 of the first embodiment will be explained.

This process performs the steps S2 and S3 of the sixth embodiment of removing the His-tagged factor 107 by using the magnetic particles 108 after the ribosome removing steps S4 to S6. In FIG. 8, like reference numerals are used when elements are identical to the corresponding elements of FIG. 6, and their explanations are omitted. In this process, too, three different methods are used in applying a force to cause the subject liquid to pass easily through the thin-film filter 19. These three methods of applying a force are [A] by manually applying a pressure to a subject, [B] by automatically applying a constant pressure to a subject and [C] by applying a centrifugal force to a subject by a centrifuge. To ensure that the three methods are performed under the same conditions, the filtration device 10 with 8-ganged air nozzles is used to process eight samples at one time. Of the eight samples, three are subjected to a force.

At step S11, a reaction solution is produced by mixing. For this purpose, the nozzle head 74 of the filter-incorporated tip processing device 70 in the filtration device 10 is moved by the X-axis drive mechanism not shown to the position of the eight pipette tips 60 accommodated in the pipette tip accommodation column 90. Then, the motor 78 for the vertical drive mechanism is started to lower all of the air nozzles 20 simultaneously to insert them into the opening portions of the pipette tips 60 for engagement. Next, the nozzle head 74 is raised by the vertical drive mechanism and then moved horizontally by the X-axis drive mechanism to the position of the target substance accommodation wells 82 in the filtration area 71, into which reagents—accommodated in the wells of the 8-ganged cartridge containers 72 and sucked into the pipettes and mixed—are pipetted so that the total volume of the reaction solution shown at step S1 will be 50 µl.

This operation is performed by cooling the target substance accommodation wells 82, as by putting ice close to them. As a result, a reaction solution containing template DNA 105, ribosome 106 and His-tagged factor 107 can be produced in the target substance accommodation wells 82, as shown in FIG. 8. The reaction solution is then sucked in and the nozzle head 74 is moved to the well column 86 that is kept at a constant temperature of 37° C. The reaction solution is then ejected into the well column 86, where it is left standing for one hour to allow the reaction to be completed to produce the target protein.

At step 12, the reaction solution is sucked in from the well column 86 and the nozzle head 74 is moved to the target substance accommodation wells 82. The reaction solution is again ejected into the target substance accommodation wells 82, which are cooled by putting ice close to them. In this state, 50 µl of nuclease free water is added to make the total volume in the wells 82 amount to 100 µl. (Three products or subjects are prepared: a product or subject 3A for which a method that manually applies a pressure is used; a product or subject 3B for which a method that performs a fully automated pressurization is used; and a product or subject 3C for which a method that applies a centrifugal force instead of pressure is used).

At step S13, the reaction solution is sucked into the pipette tips 60 and then ejected into the guide opening portion 14 of the filter-incorporated tip 11 accommodated in the filter-incorporated tip accommodation column 87. Now, the reaction solution is contained in the large-diameter tube of the filter-incorporated tip 11.

At step S14, the pipette tips 60 are forced down by the comb-shaped claw 103a and the vertical drive mechanism for disconnection from the air nozzles 20 of the nozzle head 74. After this, the air nozzles 20 are inserted into the guiding opening portions 14 of the filter-incorporated tips 11 through the adapters 21, thus fitting the filter-incorporated tips 11 over the air nozzles 20. Next, with the filter-incorporated tips 11 attached to the air nozzles 20, the nozzle head 74 is moved to the well column 88 of FIG. 5, into which the front nozzle portion 17 of the narrow tube 16 of each filter-incorporated tip 11 is inserted. In this state, the suction/ejection mechanism of the filter-incorporated tip processing device 70 is activated to eject a gas to pressureize, from above, the reaction solution in the guide tube 15, thereby forcing the reaction solution to pass through the thin-film filter 19 or ultrafiltration membrane. This step is carried out in three different ways. That is, a subject [A] undergoes a process that manually applies a non-constant pressure to the subject; a subject [B] undergoes a process that automatically applies a constant pressure to the subject; and a subject [C] undergoes a (conventional) process that applies a centrifugal force instead of pressure to the subject.

At step S15, from the wells 73, which accommodates 50 µl part of the solution that has passed through the thin-film filter 19 and the metal magnetic particles 108 (His-tagged beads: Toyobo) covered with metal affinity resin, 101*l* of the solution suspending the magnetic particles 108 is sucked in and ejected into the well column 88, in which the liquids are mixed and stirred. For mixing, a suction/ejection operation is repeated at a predetermined speed (for example, a few tens of microliters/second) for about 15 minutes.

At step S16, with the well column 88 cooled as described above, the magnets 103b of the filter-incorporated tip processing device 70 are brought close, from outside, to the pipette tips 60 mounted to the nozzle head 74 to subject them to a magnetic field. Under the influence of the magnetic field, the suction/ejection operation is performed at a predetermined speed (e.g., a few tens of microliters/second) to cause the magnetic particles 108 to adhere to the inner walls of the pipette tips for isolation (B/F isolation).

Since the magnetic particles 108 are bound with the His-tagged factors 107, the B/F isolation of the magnetic particles results in proteins other than the synthesized target protein 109 being eliminated.

At step 17, 50 µl of the top clear layer in the well column 88 is sucked into the pipette tips 60. The nozzle head 74 is moved to the well column 89, into which the 50 µl of the top clear layer is ejected and to which 50 µl of the nuclease free water is added, making the total volume in the well column 89 amount to 100 µl. (Three products or subjects are prepared: a product or subject 4A for which a method that manually applies a pressure is used; a product or subject 4B for which a method that performs a fully automated pressurization is used; and a product or subject 4C for which a method that applies a centrifugal force instead of pressure is used).

Figure 9:
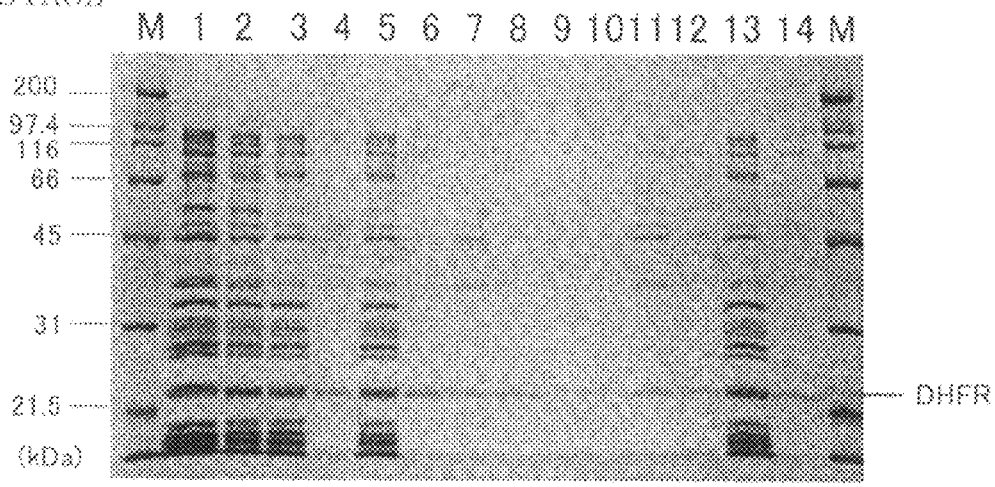
FIG. 9 shows results of filtration performed by the sixth and seventh embodiment of this invention.

FIG. 9(a) shows results of the above process for the three different methods: a method according to the sixth embodiment (manual or automated pressurization from step S1 to step S7), a method according to the seventh embodiment (manual or automated pressurization from step S11 to step S17), and a conventional method (which applies a centrifugal force to the filter-incorporated tip 11 by using the conventional centrifuge instead of applying a pressure to the filter-incorporated tip 11 in the steps S1 to S7 and steps S11 to S17). The results includes a volume of elution.

For more detailed examination of the process result of FIG. 9(a), another test result is shown in FIG. 9(b). FIG. 9(b) shows a result obtained by applying an electrophoresis method using ADS-PAGE (one of electrophoresis methods using polyacrylamide gel and performed in the presence of a surfactant SDS (sodium dodecyl sulfate or sodium lauryl sulfate). Here, lane M represents a marker indicating a molar weight of the protein of interest (in units of kilo Dalton). Lane 1 represents a case where the template DNA is not contained. Lane 2 represents a protein synthesized by the process of this embodiment. Lane 2 to lane 14 represent a process of purification after a protein has been synthesized.

Lane 3 represents the product 1A obtained when the step of removing His-tagged factor 107 was performed according to the sixth embodiment. Lane 4 represents the product 2A obtained when the His-tagged factor removing step and the pressurization step were performed according to the sixth embodiment. Lane 5 represents the product 1B obtained when the His-tagged factor removing step was performed according to the sixth embodiment. Lane 6 represents the product 2B obtained when the His-tagged factor removing step and the automated, constant pressure application step were performed according to the sixth embodiment.

Lane 7 represents the product 3A obtained when the manual pressure application was performed according to the seventh embodiment. Lane 8 represents the product 4A obtained when the manual pressure application was performed according to the seventh embodiment, followed by the His-tagged factor removing step. Lane 9 represents the product 3B obtained when the fully automated, constant pressure application was performed according to the seventh embodiment. Lane 10 represents the product 4B obtained when the fully automated, constant pressure application was performed according to the seventh embodiment, followed by the His-tagged factor removing step.

Lane 11 represents the product 3C obtained when a centrifugal force was applied by a centrifuge according to the seventh embodiment. Lane 12 represents the product 4C obtained when a centrifugal force was applied by a centrifuge according to the seventh embodiment, followed by the His-tagged factor removing step. Lane 13 represents the product 1C obtained when the His-tagged factor removing step was executed according to the sixth embodiment. Lane 14 represents the product 2C obtained when the His-tagged factor removing step was executed according to the sixth embodiment, followed by the centrifugal force application step by a centrifuge.

As shown in FIG. 9(a), comparison between the processes of the sixth and seventh embodiment shows that the automated, controlled application of a constant pressure produces a greater volume of elution than the manual application of a pressure. When the application of a constant pressure and the application of a centrifugal force are compared, almost the same amounts of elution are obtained. This shows that the application of pressure of 2.25 atom can produce the same effect as that produced by the application of a centrifugal force from a centrifuge. The amount of elution obtained by the manual pressure application is nearly 70 percent of what the application of a centrifugal force can generate. Judging from this fact, it can be seen that the device of this invention, even if used manually, can be competitively used, compared with the application of a centrifugal force.

In FIG. 9(b), comparison among the lanes 4, 6, 8, 10, 12, 14 of SDS-PAGE has found almost no difference in DHFR band density, which leads us to conclude that the purified concentrations do not differ much. Particularly, there is no difference between the application of a centrifugal force and other cases. So, it can safely be said that there is no problem with the protein purification through the pressure application. When the test was conducted in the order of the pressure application followed by the His-tagged factor elimination, other proteins than DHFR were clearly removed (lanes 8, 10, 12). Further, when the test was done in the order of the His-tagged factor elimination followed by the pressure application, there are small amounts of substances other than DHFR still remaining in the solution after purification, when compared with the process that performs the pressure application first and then the His-tagged factor elimination. However, the density of bands indicates that the execution of the His-tagged factor elimination followed by the pressure application results in a somewhat greater concentration of purified DHFR (lanes 4, 6, 14). The bands look somewhat light in lane 9 and lane 10 because the amount of synthesized DHFR is small.

Figure 10:
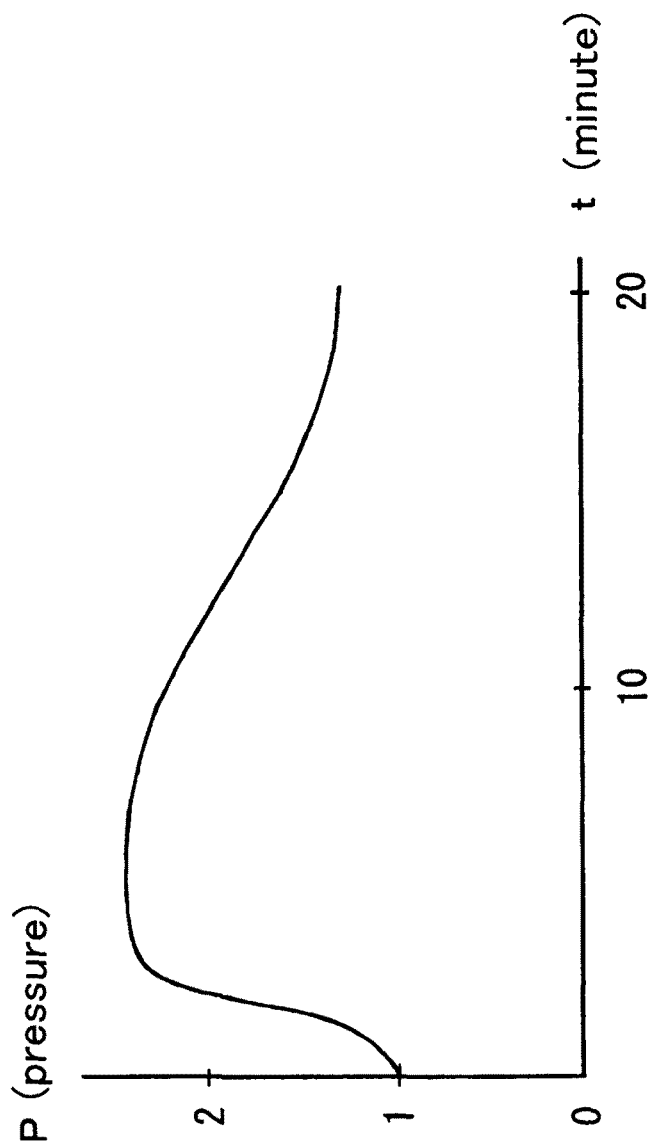
FIG. 10 shows a pressure pattern according to the sixth and seventh embodiment of this invention.

FIG. 10 shows an outline of measured pressure patterns according to the sixth or seventh embodiment. The pressure pattern represents a pressure measured on the upper side of the thin-film filter 19 in the filter-incorporated tip 11 when a gas is ejected uniformly over time. The pattern shows that the pressure reaches a maximum level and then, as the liquid passes through the filter, decreases progressively. The pressure pattern varies depending on the volume of liquid (zero before the liquid is introduced), the structure of filter, the construction of the filter-incorporated tip and the level of pressure applied.

Figure 11:
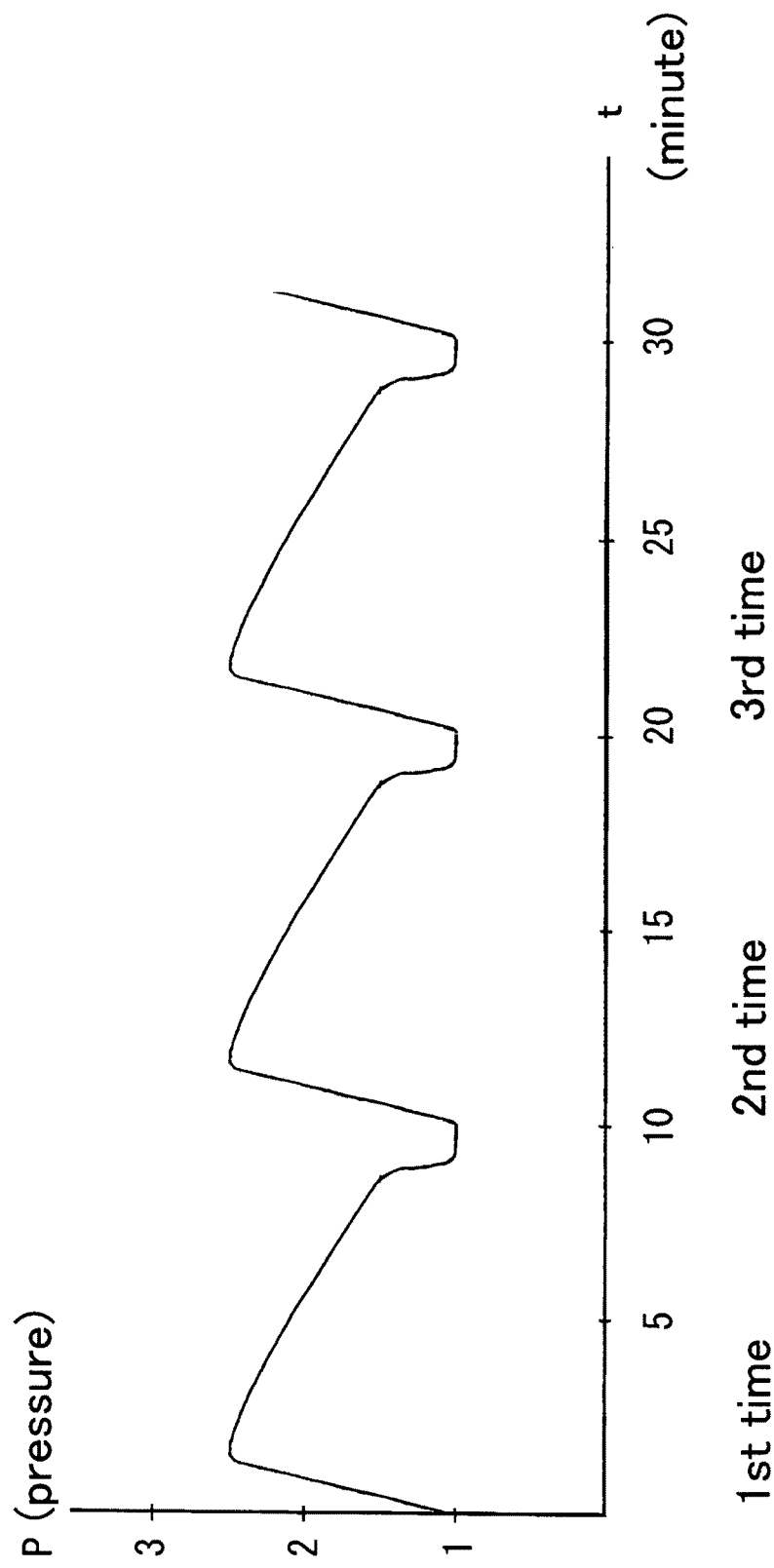
FIG. 11 shows another pressure pattern according to the sixth and seventh embodiment of this invention.

FIG. 11 shows an outline of other measured pressure patterns according to the sixth or seventh embodiment. In this example, three successive ejections of gas separated by short intervals were performed over a period of 30 minutes. The pressure pattern indicates a pressure measured on the upper side of the thin-film filter 19 in the filter-incorporated tip 11. The pressure application is therefore controlled according to a liquid volume, a target substance, a filter structure and an object of the process so that the pressure pattern will be an appropriate, predetermined value.

If a deviation from the pressure pattern is detected because of air leakage, liquid leakage or filter failure, the pressure application is stopped and the filter-incorporated tip or filter is replaced with a new one. Alternatively, the pressure application is stopped temporarily and then activated again. If any deviation from the pressure pattern is detected, the pressure application is again stopped. This procedure is repeated. The pressure (pressure pattern) measured during the pressure application may be used for controlling the pressure. For example, the control may involve keeping the measured pressure in the filter-incorporated tip constant. Replacing the filter-incorporated tip or filter may be done by drawing the liquid out of the filter-incorporated tip into a pipette tip, moving it to other location and ejecting it into a new filter-incorporated tip.

Figure 12:
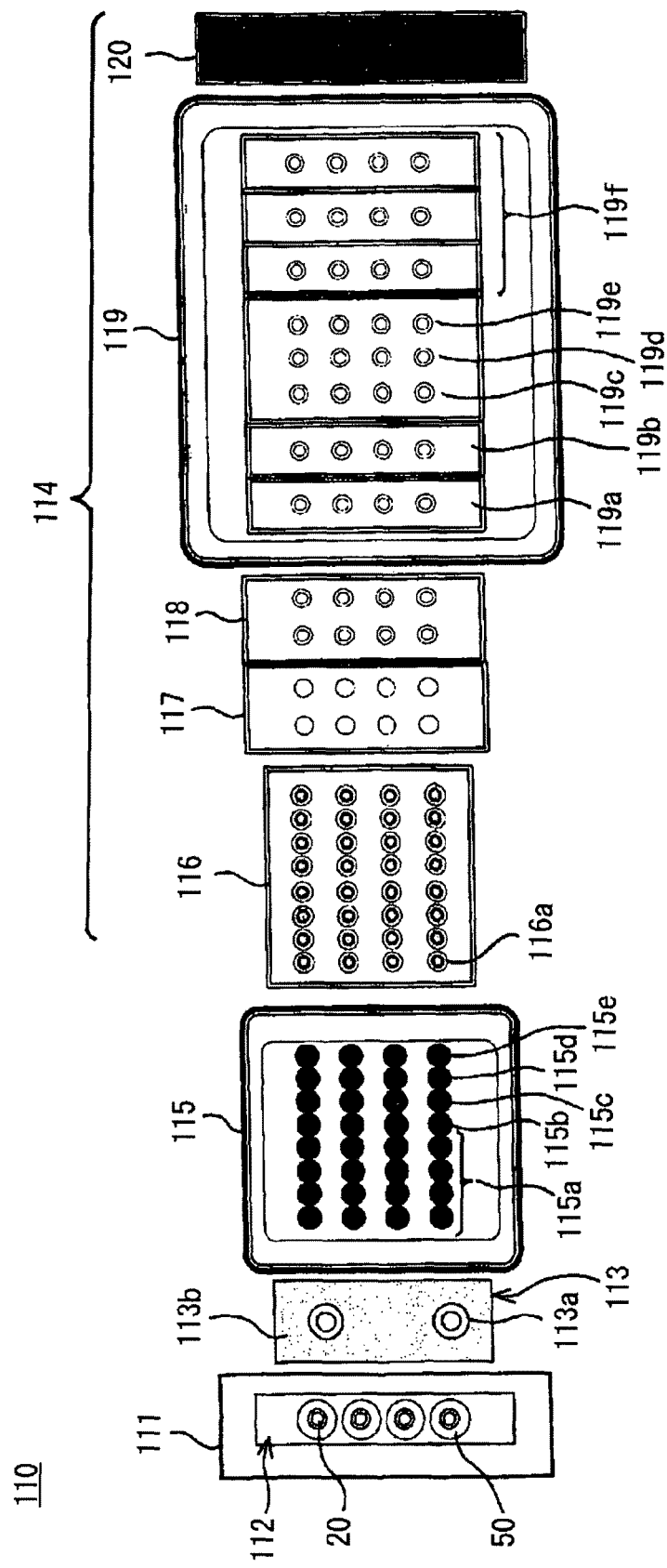
FIG. 12 is a plan view showing a filtration device according to an eighth embodiment of this invention.

Next, by referring to FIG. 12, a filtration device 110 according to an eighth embodiment of this invention will be explained. FIG. 12 shows an entire, schematic plan view of the filtration device 110.

The filtration device 110 comprises a filter-incorporated tip processing device 111 having 4-ganged air nozzles 20 each removably fitted with the filter-incorporated tip 50; an evaporation prevention cover 113; and a filtration area 114. The filtration area 114 is an area in which solutions containing a variety of samples and reagents are introduced into the filter-incorporated tips 50; in which a gas is ejected into the filter-incorporated tips 50 to cause liquids to pass through the filter; in which products obtained by the filtration are accommodated; in which operations, such as pipetting, stirring, washing, extraction, transfer and reaction, are performed to prepare solutions to be introduced; or in which a variety of reagents, mixed liquids, solutions, reactive liquids or samples are accommodated. When the filter-incorporated tip 50 or pipette tip 60 is fitted in an engagement cylinder 113a of the platelike evaporation prevention cover 113, other air nozzles 20 of an air nozzle head 112 are not fitted with the filter-incorporated tip 50 or pipette tip 60.

The evaporation prevention cover 113 comprises a rectangular plate 113b and two engagement cylinders 113a which are situated at positions corresponding to two end air nozzles 20 of the four-ganged air nozzles 20 and which are sized to fit over the air nozzles 20. The evaporation prevention cover 113, when fitted to the air nozzles 20, can be moved together with the air nozzle head 112. So, the evaporation prevention cover 113 can close the opening portion of the associated wells during incubation to prevent evaporation. The evaporation prevention cover 113 can be attached to and detached from the air nozzles 20 by the comb-shaped claw 103a and the vertical drive mechanism, both combining to constitute a mechanism for coupling or decoupling the filter-incorporated tips or pipette tips. For engagement, the air nozzles 20 are lowered into the engagement cylinders 113a by the vertical drive mechanism.

The filtration area 114 comprises: a product container 115 having wells arranged in a 8×4 matrix for accommodating products; a pipette tip accommodation portion 116 having a holder portion 116a for accommodating pipette tips in a 8×4 arrangement matrix, the pipette tips being adapted to be fitted over the air nozzles 20 for pipetting, stirring, washing, extraction and transfer; an adapter accommodation portion 117 having a holder portion for accommodating the adapters 21 in a 2×4 arrangement matrix, the adapters 21 being adapted to be fitted over the air nozzles 20; a filter-incorporated tip accommodation portion 118 having a holder portion for accommodating the filter-incorporated tips 50 in a 2×4 arrangement matrix; a reagent accommodation portion 119 having tubes arranged in a 8×4 matrix for accommodating reagents used to prepare a solution, the solution being adapted to be introduced into and processed by the filter-incorporated tip 50; and a tip discarding port 120.

In the product container 115, a 4×4 matrix of wells constitute a product container 115a for accommodating a purified, target protein. A next 1×4 matrix of wells constitute a B/F isolated reaction liquid accommodation portion 115b for accommodating the reaction liquid that has undergone the B/F isolation by nickel beads as the magnetic particles. A next 1×4 matrix of wells is a magnetic particle reaction bath 115c for allowing a reaction to be carried out by using nickel beads as the magnetic particles. A next 1×4 matrix of wells is a magnetic particle washing bath 115d for cleaning the magnetic particles. A next 1×4 matrix of wells is a temperature-controllable incubation bath 115e for executing an incubation.

In the reagent accommodation portion 119, a 1×4 matrix of tubes is a product collecting tube column 119a to collect products that are produced by executing the pressure application operation on the filter-incorporated tips 50 with their front nozzle portions inserted into or disposed above the product collecting tube column 119a. A next 1×4 matrix of tubes is a pressurization sample tube column 119b to accommodate samples to which a pressure is to be applied. A next 1×4 matrix of tubes is a magnetic particle accommodation tube column 119c to accommodate reagents or substances, such as nickel beads as the magnetic particles, necessary for generating the pressurization sample. A next 1×4 matrix of tubes is a sterilizing water accommodation portion 119d to accommodate a sterilizing water (nuclease free water). A next 1×4 matrix of tubes is a template DNA accommodation portion 119e. A next 3×4 matrix of tubes is a reagent accommodation portion 119f to accommodate a variety of reagents.

As described above, the process of this embodiment enables a target substance to be reliably produced by a fine control using a small device without having to use a conventional centrifuge, which in turn allows for a highly efficient protein purification at low cost.

The preceding explanations concern a case where three air nozzles are used on the filter-incorporated tip 11. It is also possible to use any desired number of air nozzles and thus execute a plurality of processes at one time. Therefore, the process of this embodiment makes it possible to handle many samples simultaneously with a small device, realizing a high efficiency.

The preceding embodiments have been described only by way of example to facilitate understanding and do not limit the present invention in any way. Thus various modifications and changes may be made without departing from the spirit of this invention. For example, although the preceding embodiments have explained mainly about a case of protein purification, the target substance may be DNA substances, RNA or sugar chain. Further, although the filter has been described to be formed like a thin film, a thin plate or a block (cylinder), it may be formed like a rectangular parallelepiped. This invention can also be applied to amorphous filters. It should also be noted that this invention is not limited to any particular values, the number of times, shapes, the number of parts and volumes that have appeared in the above description.

Various constituent elements, individual filter-incorporated tips, filters, tip-shaped containers, locking portions, air nozzles, heating means and other devices may be changed in shape as required and arbitrarily combined for use. Further, biological substances include genetic substances, such as DNA, oligonucleotide and RNA, immunosubstances, proteins, sugar chains, pheromone, allomone, mitochondria, virus and plasmid. The reagents and substances described above are only examples and other reagents and substances can be used.

The present invention relates to a filter-incorporated tip, a filtration device and a filtration method. This invention concerns a wide range of fields that require handling of biological polymers, including genes, immunosubstances, amino acids, proteins and sugars, and biological monomers. Among them are industrial fields, agricultural fields such as food, agriculture and processing of marine products, pharmaceutical fields, medical fields including hygiene, health, immunity, disease and genetics, and science fields such as chemistry and biology. The present invention is particularly advantageous where a series of processing steps using a large number of reagents and substances are executed successively in a predetermined order.

The invention claimed is:

1. A filtration method comprising:
   a liquid introducing step to introduce a liquid into a filter-incorporated tip through a guide opening portion thereof,
   wherein the filter-incorporated tip has a nozzle-tipped container and a filter, the nozzle-tipped container has a guide opening portion that can be directly or indirectly fitted to an air nozzle capable of ejecting a gas and a front nozzle portion capable of delivering the liquid by the ejection of the gas from the air nozzle, and the filter is locked in the nozzle-tipped container to partition the interior of the nozzle-tipped container into the guide opening portion side and the front nozzle portion side and can temporarily hold the liquid and isolate a predetermined substance as the liquid passes through the filter, when the nozzle-tipped container is coupled to the air nozzle on the guide opening portion side;

a coupling step to directly or indirectly couple the filter-incorporated tip containing the liquid to the air nozzle;
a pressure application step to eject the gas from the air nozzle into the coupled filter-incorporated tip; and
a preprocessing step to process the liquid using a pipette tip fitted to the air nozzle before the liquid introducing step, the air nozzle being capable of performing a suction of gas in addition to the ejection;
wherein the liquid introducing step comprises introducing the liquid into the filter-incorporated tip using the pipette tip; and
wherein the coupling step comprises removing the pipette tip from the air nozzle and then directly or indirectly coupling the filter-incorporated tip to the air nozzle.

2. A filtration method according to claim 1, wherein a pressure application in the pressure application step that depends on the volume of gas ejected from the air nozzle, gas pressure, speed, the number of ejections, time or position is controlled according to a construction of the air nozzle, a member fitted to the air nozzle or the filter-incorporated tip, according to physical conditions including a kind of substance present in the liquid, a density of the substance, a volume of the liquid and a coordinate position including liquid accommodation position, and according to a content of the process to be performed.

3. A filtration method according to claim 2, wherein the pressure applied through the air nozzle in the pressure application step is constant over time.

4. A filtration method according to claim 1, further including:
a pressure pattern measuring step to directly or indirectly couple the filter-incorporated tip to the air nozzle, eject the gas from the air nozzle into the into the coupled filter-incorporated tip, and measure a pressure pattern of the filter-incorporated tip before the liquid introducing step or during the pressure application step.

5. A filter-incorporated device comprising:
an air nozzle capable of ejecting and suctioning a gas;
a nozzle-tipped container having a guide opening portion directly or indirectly coupled to the air nozzle, and a front nozzle portion capable of delivering a liquid by the ejection or suction of the gas by the air nozzle, with engaging or screwing; and
a filter locked in the nozzle-tipped container to partition the interior of the nozzle-tipped container into the guide opening portion side and the front nozzle portion side, wherein the filter can temporarily hold the liquid being introduced using the pipette tip fitted to the air nozzle through the guide opening portion and isolate a predetermined substance as the liquid passes through the filter, with the nozzle-tipped container coupled to the air nozzle on the guide opening portion side.

6. A filter-incorporated device according to claim 5, wherein the nozzle-tipped container comprises:
a large-diameter tube;
a small-diameter tube provided below the large-diameter tube and formed narrower than the large-diameter tube; and
a transition portion provided between the large diameter tube and the small-diameter tube;
wherein the guide opening portion is provided at an upper end of the large-diameter tube;
wherein the front nozzle portion is provided at a front end of the small-diameter tube.

7. A filter-incorporated tip according to claim 6, wherein the nozzle-tipped container has a filter locking portion to lock the filter in the nozzle-tipped container so that the liquid introduced into the nozzle-tipped container can come into contact with the filter.

8. A filter-incorporated tip according to claim 6, wherein the filter locking portion has one or more filter support members provided separate from the nozzle-tipped container so that the filter support members can partition the interior of the nozzle-tipped container into the front nozzle portion side and the guide opening portion side.

9. A filter-incorporated device according to claim 5, wherein the nozzle-tipped container has a filter locking portion to lock the filter in the nozzle-tipped container so that the liquid introduced into the nozzle-tipped container can come into contact with the filter.

10. A filter-incorporated device according to claim 9, wherein the locking portion has between the guide opening portion and the front nozzle portion a protruding portion protruding inwardly from an inner wall surface of the nozzle-tipped container, an inclined surface or a step;
wherein the protruding portion, the inclined surface or the step hold the filter or the filter support members by locking them in the nozzle-tipped container.

11. A filter-incorporated device according to claim 5, wherein the filter locking portion has one or more filter support members provided separate from the nozzle-tipped container so that the filter support members can partition the interior of the nozzle-tipped container into the front nozzle portion side and the guide opening portion side.

12. A filter-incorporated tip according to claim 11, wherein the locking portion has between the guide opening portion and the front nozzle portion a protruding portion protruding inwardly from an inner wall surface of the nozzle-tipped container, an inclined surface or a step;
wherein the protruding portion, the inclined surface or the step hold the filter or the filter support members by locking them in the nozzle-tipped container.

13. A filter-incorporated device according to claim 5, wherein the nozzle-tipped container has a guide tube with the guide opening portion and a filter locking tube provided below and communicating with the guide tube and having the front nozzle portion at a lower end thereof;
wherein the filter is provided in the filter locking tube above the front nozzle portion to partition the interior of the filter locking tube into the guide tube side and the front nozzle portion side;
wherein the guide tube and the filter locking tube are removably connected with each other.

14. A filter-incorporated device according to claim 13, wherein the guide tube has a large-diameter tube;
wherein the filter locking tube has a small-diameter tube formed narrower than the large-diameter tube and a transition portion provided between the large-diameter tube and the small-diameter tube.

15. A filtration device comprising:
an air nozzle head having one or more-ganged air nozzles to perform suction and ejection of a gas;
a suction/ejection mechanism to perform the suction/ejection of gas through the air nozzle;
one or more filter-incorporated tips directly or indirectly connected or connectable to the air nozzle and having a filter locked therein, wherein the filter can isolate a target substance as a liquid passes through the filter;
one or more pipette tips capable of being fitted to the air nozzle;
a stage having arranged thereon a group of liquid accommodation portions accommodating or capable of accommodating a variety of liquids;

a drive means to move the air nozzle head relative to the liquid accommodation portions; and a control unit to control at least the following: a suction and ejection volume to and from the air nozzle, a pressure, a speed, the number of suction or ejection operations, and the suction or ejection position, in accordance with a construction of the air nozzle, and also to control a member fitted to the air nozzle or the filter-incorporated tip, in accordance with at least the following: a kind of substance present in the liquid, a density of the substance, and a volume of the liquid, wherein the air nozzle has a pressure sensor;

wherein the control unit performs control based on a pressure pattern detected by the pressure sensor, the pressure pattern reflecting a plurality of pressure measurements taken over a period of time; and wherein the filter-incorporated tips and the pipette tips are provided on the stage so as to be able to be engaged by inserting the air nozzle from above into respective guide opening portions of the filter-incorporated tips.

16. A filtration device according to claim 15, wherein the stage has an evaporation prevention cover comprising a plate and at least two engagement cylinders protruding upward from an upper side of the plate and provided at positions corresponding to the nozzle positions of the nozzle head, wherein the engagement cylinders can engage the nozzles and, in the engaged state, be moved by the drive means.

* * * * *

UNITED STATES PATENT AND TRADEMARK OFFICE
CERTIFICATE OF CORRECTION

PATENT NO. : 8,414,778 B2  
APPLICATION NO. : 11/920707  
DATED : April 9, 2013  
INVENTOR(S) : Hideji Tajima et al.

Page 1 of 1

It is certified that error appears in the above-identified patent and that said Letters Patent is hereby corrected as shown below:

In the Specifications

Column 20, line 13, change "pressureize" to -- pressurize --.

In the Claims

Column 25, line 66, Claim 7, change "tip" to -- device --;
change "claim 6" to -- claim 5 --.

Column 26, line 4, Claim 8, change "tip" to -- device --;
change "claim 6" to -- claim 5 --.

Column 26, line 10, Claim 9, change "claim 5" to -- claim 6 --.

Column 26, line 15, Claim 10, change "claim 9" to -- claim 7 --.

Column 26, line 23, Claim 11, change "claim 5" to -- claim 6 --.

Column 26, line 29, Claim 12, change "claim 11" to -- claim 8 --.

Signed and Sealed this
First Day of April, 2014

Michelle K. Lee
*Deputy Director of the United States Patent and Trademark Office*